US006413514B1

(12) United States Patent
Aruffo et al.

(10) Patent No.: US 6,413,514 B1
(45) Date of Patent: Jul. 2, 2002

(54) METHODS OF USING ANTIBODIES AGAINST HUMAN CD40

(75) Inventors: Alejandro A. Aruffo, Belle Mead, NJ (US); Diane Hollenbaugh, Newton, PA (US); Anthony W. Siadak, Seattle, WA (US); Karen K. Berry, Princeton, NJ (US); Linda Harris, Seattle, WA (US); Barbara A. Thorne, Issaquah, WA (US); Jurgen Bajorath, Lynnwood, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/466,635

(22) Filed: Dec. 17, 1999

Related U.S. Application Data

(62) Division of application No. 09/026,291, filed on Feb. 19, 1998, now Pat. No. 6,051,228.

(51) Int. Cl.[7] ....................... A61K 39/395; C07K 16/28
(52) U.S. Cl. ................. 424/144.1; 424/130.1; 424/133.1; 424/141.1; 424/143.1; 424/153.1; 424/173.1; 530/387.1; 530/387.3; 530/388.1; 530/388.2; 530/388.22; 530/388.7; 530/388.73
(58) Field of Search .................. 424/130.1, 133.1, 424/144.1; 530/387.1, 388.2, 388.73

(56) References Cited

PUBLICATIONS

Waltze et al. Transplantation 65: 512 (1998).*
Datta et al. Arthritis and Rheumatism 40: 1735–1745 (1997).*
Boon et al. Journal of Immunology 167: 2942–2949 (2001).*
Stuart et al. Laboratory Investigation 54:1–3 (1996).*
Kahan Cur. Opin. Immunol. 4:553–560(1992).*
Bach Tips 14: 213–216 (1993).*
Gray et al. J Exp Med 180: 141–155 (1994).*
Stuber et al. J Exp Med 183: 693–698 (1996).*
Resetkova et al. Thyroid 6: 267–273 (1996).*
Biacone et al. Kidney Int. 48: 458–468(1995).*
Larsen et al. Transplantation 661: 4–9 1996).*
Buhlmann et al. J Clin. Immunol. 16: 83–89 (1996).*
Biogen Press Release Nov. 2, 1999.*
Biogen Press Release Oct. 21, 1999.*
Seachrist BioWorld Today 10(204): 1, 3 Oct. 25, 1999.*
IDEC Press Release Apr. 20, 2000.*
Swandorg et al. Clinical Immunology and Pathology 77: 4–13 (1995).*
Stuart et al. Laboratory Investigation 54: 1–3 (1986).*

* cited by examiner

Primary Examiner—Phillip Gambel
(74) Attorney, Agent, or Firm—Joan E. Switzer

(57) ABSTRACT

A method for the treatment of T cell mediated disorders is described. The method involves administering to a subject a therapeutically effective amount of an anti-human CD40 antibody. Disease states suitable for treatment with this method include graft versus host disease and transplant rejection and auto immune disease such as type I diabetes, psoriasis, multiple sclerosis, rheumatoid arthritis, systemic lupus erythematosus, and myesthenia gravis.

10 Claims, 18 Drawing Sheets

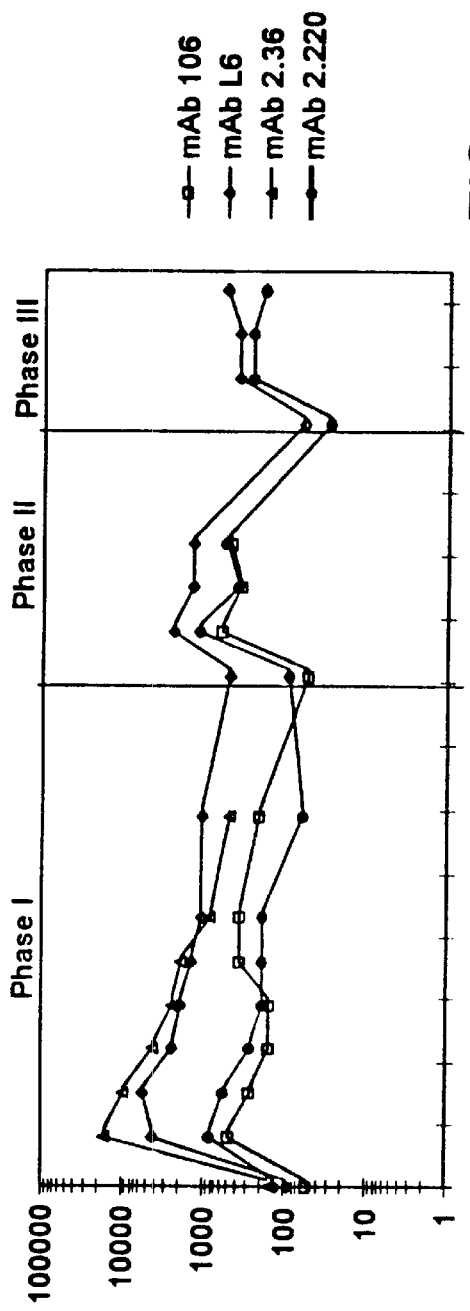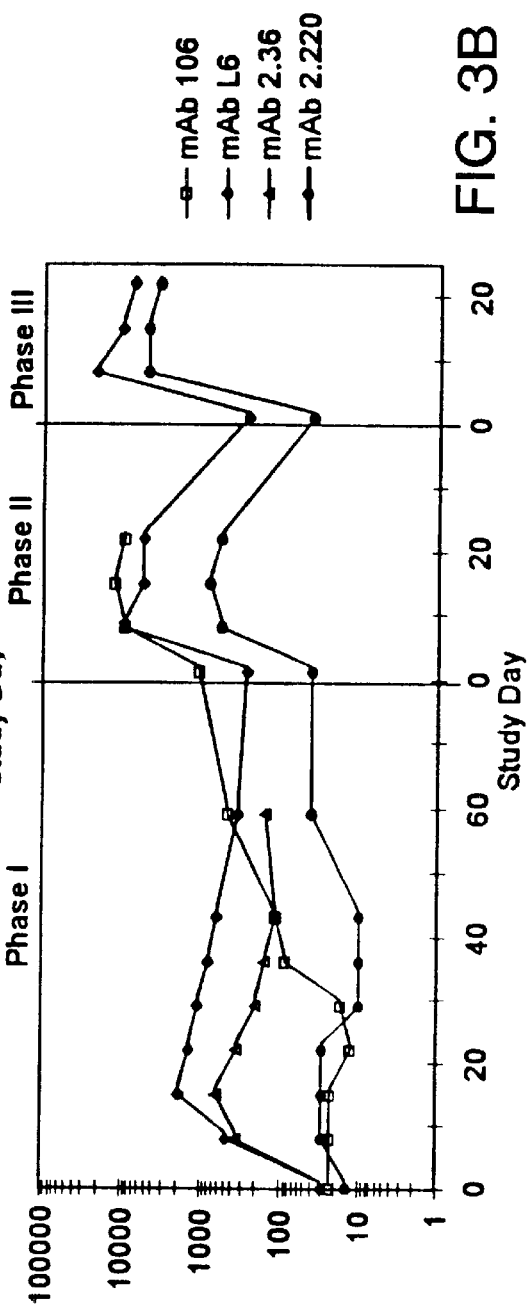

A) Light Chain Variable Region (SEQ ID NO:1).

MEAPAQLLFLLLLWLPDTTGDIVLTQSPATLSVTPGDRVSLSCRASQSISDYLHWYQQKS
HESPRLLIKYASHSISGIPSRFSGSGSGSDFTLSINSVEPEDVGIYYCQHGHSFPWTFGG
GTKLEIKR

B) Heavy Chain Variable Region (SEQ ID NO:2).

MDWTWRILFLVAAATGAHSQIQLVQSGPELKKPGETVRISCKASGYAFTTTGMQWVQEMP
GKGLKWIGWINTHSGVPKYVEDFKGRFAFSLETSANTAYLQISNLKNEDTATYFCVRSGN
GNYDLAYFAYWGQGTLVTVSA

FIG. 4

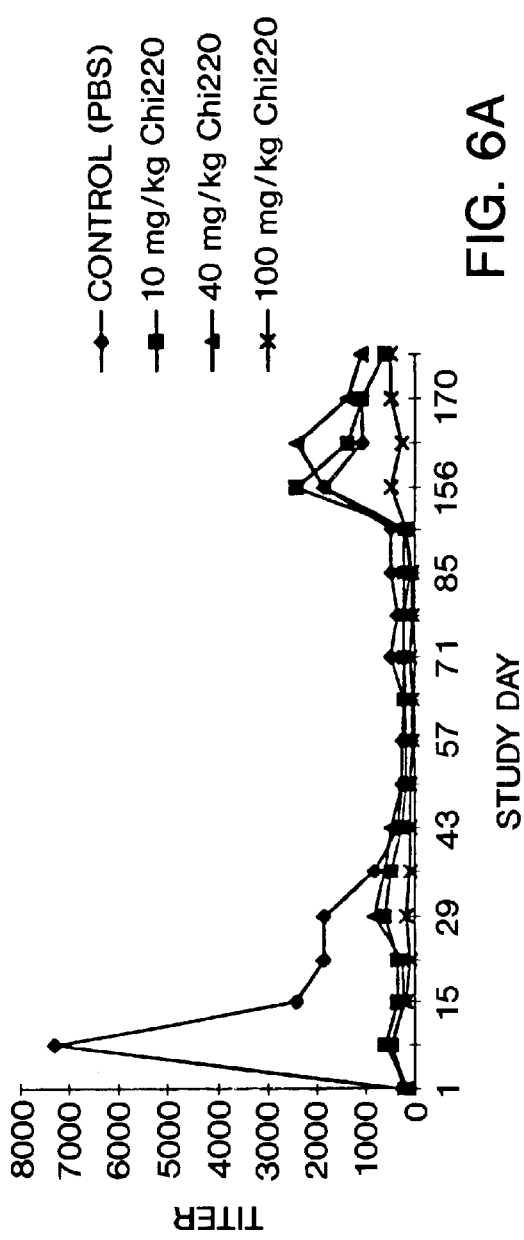
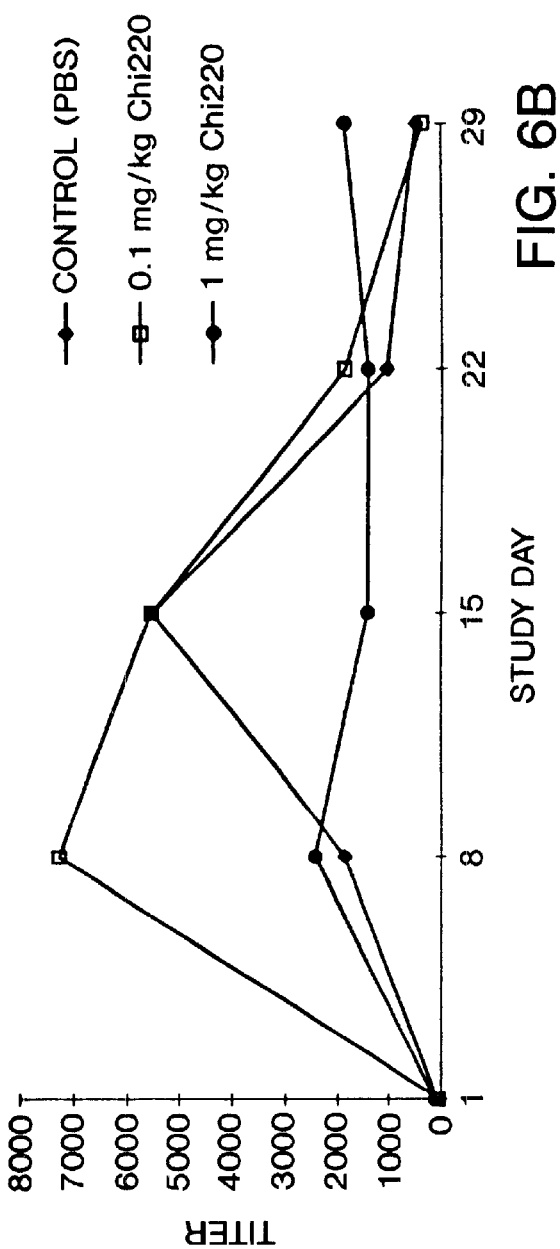

```
   1  GACGGATCGG GAGATCTGCT AGGTGACCTG AGGCGCGCCG GCTTCGAATA GCCAGAGTAA
  61  CCTTTTTTTT TAATTTTATT TTATTTTATT TTTGAGATGG AGTTTGGCGC CGATCTCCCG
 121  ATCCCCTATG GTCGACTCTC AGTACAATCT GCTCTGATGC CGCATAGTTA AGCCAGTATC
 181  TGCTCCCTGC TTGTGTGTTG GAGGTCGCTG AGTAGTGCGC GAGCAAAATT TAAGCTACAA
 241  CAAGGCAAGG CTTGACCGAC AATTGCATGA AGAATCTGCT TAGGGTTAGG CGTTTTGCGC
 301  TGCTTCGCGA TGTACGGGCC AGATATACGC GTTGACATTG ATTATTGACT AGTTATTAAT
 361  AGTAATCAAT TACGGGGTCA TTAGTTCATA GCCCATATAT GGAGTTCCGC GTTACATAAC
 421  TTACGGTAAA TGGCCCGCCT GGCTGACCGC CCAACGACCC CCGCCCATTG ACGTCAATAA
 481  TGACGTATGT TCCCATAGTA ACGCCAATAG GGACTTTCCA TTGACGTCAA TGGGTGGACT
 541  ATTTACGGTA AACTGCCCAC TTGGCAGTAC ATCAAGTGTA TCATATGCCA AGTACGCCCC
 601  CTATTGACGT CAATGACGGT AAATGGCCCG CCTGGCATTA TGCCCAGTAC ATGACCTTAT
 661  GGGACTTTCC TACTTGGCAG TACATCTACG TATTAGTCAT CGCTATTACC ATGGTGATGC
 721  GGTTTTGGCA GTACATCAAT GGGCGTGGAT AGCGGTTTGA CTCACGGGGA TTTCCAAGTC
 781  TCCACCCCAT TGACGTCAAT GGGAGTTTGT TTTGGCACCA AAATCAACGG GACTTTCCAA
 841  AATGTCGTAA CAACTCCGCC CCATTGACGC AAATGGGCGG TAGGCGTGTA CGGTGGGAGG
 901  TCTATATAAG CAGAGCTCTC TGGCTAACTA GAGAACCCAC TGCTTACTGG CTTATCGAAA
 961  TTAATACGAC TCACTATAGG GAGACCCAAG CTTGGTACCA TGGACTGGAC CTGGAGAATC
1021  CTCTTCTTGA TGGCAGCAGC AACAGTGCC CACTCCAGA TCCAGTTGGT GCAATCTGGA
1081  CCTGAGCTGA AGAAGCCTGG AGAGACAGTC AGGATCTCCT GCAAGGCTTC TGGGTATGCC
1141  TTCACAACTA CTGGAATGCA GTGGGTGCAA GAGATGCCAG GAAAGGGTTT GAAGTGGATT
1201  GGCTGGATAA ACACCCACTC TGGAGTGCCA AAATATGTAG AAGACTTCAA GGGACGGTTT
1261  GCCTTCTCTT TGGAAACCTC TGCCAACACT GCATATTTAC AGATAAGCAA CCTCAAAAAT
1321  GAGGACACGG CTACGTATTT CTGTGTGAGA TCCGGGAATG GTAACTATGA CCTGGCCTAC
1381  TTTGCTTACT GGGGCCAAGG GACACTGGTC ACTGTCTCTG CAGCTAGCAC CAAGGGCCCA
1441  TCGGTCTTCC CCCTGGCACC CTCCTCCAAG AGCACCTCTG GGGGCACAGC GGCCCTGGGC
1501  TGCCTGGTCA AGGACTACTT CCCCGAACCG GTGACGGTGT CGTGGAACTC AGGCGCCCTG
1561  ACCAGCGGCG TGCACACCTT CCCGGCTGTC CTACAGTCCT CAGGACTCTA CTCCCTCAGC
1621  AGCGTGGTGA CCGTGCCCTC CAGCAGCTTG GGCACCCAGA CCTACATCTG CAACGTGAAT
1681  CACAAGCCCA GCAACACCAA GGTGGACAAG AAAGTTGGTG AGAGGCCAGC ACAGGGAGGG
1741  AGGGTGTCTG CTGGAAGCCA GGCTCAGCGC TCCTGCCTGG ACGCATCCCG GCTATGCAGC
1801  CCCAGTCCAG GGCAGCAAGG CAGGCCCCGT CTGCCTCTTC ACCCGGAGGC CTCTGCCCGC
1861  CCCACTCATG CTCAGGGAGA GGGTCTTCTG GCTTTTTCCC CAGGCTCTGG GCAGGCACAG
1921  GCTAGGTGCC CCTAACCCAG GCCCTGCACA CAAAGGGGCA GGTGCTGGGC TCAGACCTGC
1981  CAAGAGCCAT ATCCGGGAGG ACCCTGCCCC TGACCTAAGC CCACCCCAAA GGCCAAACTC
2041  TCCACTCCCT CAGCTCGGAC ACCTTCTCTC CTCCCAGATT CCAGTAACTC CCAATCTTCT
2101  CTCTGCAGAG CCCAAATCTT GTGACAAAAC TCACACATGC CCACCGTGCC CAGGTAAGCC
2161  AGCCCAGGCC TCGCCCTCCA GCTCAAGGCG GGACAGGTGC CCTAGAGTAG CCTGCATCCA
2221  GGGACAGGCC CCAGCCGGGT GCTGACACGT CCACCTCCAT CTCTTCCTCA GCACCTGAAC
2281  TCCTGGGGGG ACCGTCAGTC TTCCTCTTCC CCCCAAAACC CAAGGACACC CTCATGATCT
2341  CCCGGACCCC TGAGGTCACA TGCGTGGTGG TGGACGTGAG CCACGAAGAC CCTGAGGTCA
2401  AGTTCAACTG GTACGTGGAC GGCGTGGAGG TGCATAATGC CAAGACAAAG CCGCGGGAGG
2461  AGCAGTACAA CAGCACGTAC CGTGTGGTCA GCGTCCTCAC CGTCCTGCAC CAGGACTGGC
2521  TGAATGGCAA GGAGTACAAG TGCAAGGTCT CCAACAAAGC CCTCCCAGCC CCCATCGAGA
2581  AAACCATCTC CAAAGCCAAA GGTGGGACCC GTGGGGTGCG AGGGCCACAT GGACAGAGGC
2641  CGGCTCGGCC CACCCTCTGC CCTGAGAGTG ACCGCTGTAC CAACCTCTGT CCCTACAGGG
2701  CAGCCCCGAG AACCACAGGT GTACACCCTG CCCCCATCCC GGGATGAGCT GACCAAGAAC
2761  CAGGTCAGCC TGACCTGCCT GGTCAAAGGC TTCTATCCCA GCGACATCGC CGTGGAGTGG
2821  GAGAGCAATG GGCAGCCGGA GAACAACTAC AAGACCACGC CTCCCGTGCT GGACTCCGAC
2881  GGCTCCTTCT TCCTCTACAG CAAGCTCACC GTGGACAAGA GCAGGTGGCA GCAGGGGAAC
2941  GTCTTCTCAT GCTCCGTGAT GCATGAGGCT CTGCACAACC ACTACACGCA GAAGAGCCTC
3001  TCCCTGTCTC CGGGTAAATG AGTGCGACGG CCGGCAAGCC CCCGCTCCCC GGGCTCTCGC
```

FIG. 13A

```
3061 GGTCGCACGA GGATGCTTGG CACGTACCCC CTGTACATAC TTCCCGGGCG CCCAGCATGG
3121 AAATAAAGCA CCCAGCGCTG CCCTGGGCCC CTGCGAGACT GTGATGGTTC TTTCCACGGG
3181 TCAGGCCGAG TCTGAGGCCT GAGTGGCATG AGGGAGGCAG AGCGGGTCCC ACTGTCCCCA
3241 CACTGGCCCA GGCTGTGCAG GTGTGCCTGG GCCCCTAGG GTGGGGCTCA GCCAGGGGCT
3301 GCCCTCGGCA GGGTGGGGGA TTTGCCAGCG TGGCCCTCCC TCCAGCAGCA CCTGCCCTGG
3361 GCTGGGCCAC GGGAAGCCCT AGGAGCCCCT GGGGACAGAC ACACAGCCCC TGCCTCTGTA
3421 GGAGACTGTC CTGTTCTGTG AGCGCCCTG TCCTCCCGAC CTCCATGCCC ACTCGGGGGC
3481 ATGCCTAGTC CATGTGCGTA GGGACAGGCC CTCCCTCACC CATCTACCCC CACGGCACTA
3541 ACCCCTGGCT GCCCTGCCCA GCCTCGCACC CGCATGGGGA CACAACCGAC TCCGGGGACA
3601 TGCACTCTCG GGCCCTGTGG AGGGACTGGT GCAGATGCCC ACACACACAC TCAGCCCAGA
3661 CCCGTTCAAC AAACCCCGCA CTGAGGTTGG CCGGCACAC GGCCACCACA CACACACGTG
3721 CACGCCTCAC ACACGGAGCC TCACCCGGGC GAACTGCACA GCACCCAGAC CAGAGCAAGG
3781 TCCTCGCACA CGTGAACACT CCTCGGACAC AGGCCCCCAC GAGCCCACG CGGCACCTCA
3841 AGGCCCACGA GCCTCTCGGC AGCTTCTCCA CATGCTGACC TGCTCAGACA AACCCAGCCC
3901 TCCTCTCACA AGGGTGCCCC TGCAGCCGCC ACACACACAC AGGGGATCAC ACACCACGTC
3961 ACGTCCCTGG CCCTGGCCCA CTTCCCAGTG CCGCCCTTCC CTGCAGGACG GATCAGCCTC
4021 GACTGTGCCT TCTAGTTGCC AGCCATCTGT TGTTTGCCCC TCCCCGTGC CTTCCTTGAC
4081 CCTGGAAGGT GCCACTCCCA CTGTCCTTTC CTAATAAAT GAGGAAATTG CATCGCATTG
4141 TCTGAGTAGG TGTCATTCTA TTCTGGGGGG TGGGGTGGGG CAGGACAGCA AGGGGGAGGA
4201 TTGGGAAGAC AATAGCAGGC ATGCTGGGGA TGCGGTGGGC TCTATGGCTT CTGAGGCGGA
4261 AAGAACCAGC TGGGGCTCTA GGGGGTATCC CCACGCGCCC TGTAGCGGCG CATTAAGCGC
4321 GGCGGGTGTG GTGGTTACGC GCAGCGTGAC CGCTACACTT GCCAGCGCCC TAGCGCCCGC
4381 TCCTTTCGCT TTCTTCCCTT CCTTTCTCGC CACGTTCGCC GGGCCTCTCA AAAAAGGGAA
4441 AAAAAGCATG CATCTCAATT AGTCAGCAAC CATAGTCCCG CCCTAACTC CGCCCATCCC
4501 GCCCCTAACT CCGCCCAGTT CCGCCCATTC TCCGCCCCAT GGCTGACTAA TTTTTTTTAT
4561 TTATGCAGAG GCCGAGGCCG CCTCGGCCTC TGAGCTATTC CAGAAGTAGT GAGGAGGCTT
4621 TTTTGGAGGC CTAGGCTTTT GCAAAAAGCT TGGACAGCTC AGGGCTGCGA TTTCGCGCCA
4681 AACTTGACGG CAATCCTAGC GTGAAGGCTG GTAGGATTTT ATCCCGCTG CCATCATGGT
4741 TCGACCATTG AACTGCATCG TCGCCGTGTC CCAAAATATG GGGATTGGCA AGAACGGAGA
4801 CCTACCCTGG CCTCCGCTCA GGAACGAGTT CAAGTACTTC CAAAGAATGA CCACAACCTC
4861 TTCAGTGGAA GGTAAACAGA ATCTGGTGAT TATGGGTAGG AAAACCTGGT TCTCCATTCC
4921 TGAGAAGAAT CGACCTTTAA AGGACAGAAT TAATATAGTT CTCAGTAGAG AACTCAAAGA
4981 ACCACCACGA GGAGCTCATT TTCTTGCCAA AAGTTTGGAT GATGCCTTAA GACTTATTGA
5041 ACAACCGGAA TTGGCAAGTA AAGTAGACAT GGTTTGGATA GTCGGAGGCA GTTCTGTTTA
5101 CCAGGAAGCC ATGAATCAAC CAGGCCACCT TAGACTCTTT GTGACAAGGA TCATGCAGGA
5161 ATTTGAAAGT GACACGTTTT TCCCAGAAAT TGATTGGGG AAATATAAAC TTCTCCCAGA
5221 ATACCCAGGC GTCCTCTCTG AGGTCCAGGA GGAAAAAGGC ATCAAGTATA AGTTTGAAGT
5281 CTACGAGAAG AAAGACTAAC AGGAAGATGC TTTCAAGTTC TCTGCTCCCC TCCTAAAGCT
5341 ATGCATTTTT ATAAGACCAT GGGACTTTTG CTGGCTTTAG ATCTCTTTGT GAAGGAACCT
5401 TACTTCTGTG GTGTGACATA ATTGGACAAA CTACCTACAG AGATTTAAAG CTCTAAGGTA
5461 AATATAAAAT TTTTAAGTGT ATAATGTGTT AAACTACTGA TTCTAATTGT TTGTGTATTT
5521 TAGATTCCAA CCTATGAAC TGATGAATGG GAGCAGTGGT GGAATGCCTT TAATGAGGAA
5581 AACCTGTTTT GCTCAGAAGA AATGCCATCT AGTGATGATG AGGCTACTGC TGACTCTCAA
5641 CATTCTACTC CTCCAAAAAA GAAGAGAAAG GTAGAAGACC CCAAGGACTT TCCTTCAGAA
5701 TTGCTAAGTT TTTTGAGTCA TGCTGTGTTT AGTAATAGAA CTCTTGCTTG CTTTGCTATT
5761 TACACCACAA AGGAAAAAGC TGCACTGCTA TACAAGAAAA TTATGGAAAA ATATTCTGTA
5821 ACCTTTATAA GTAGGCATAA CAGTTATAAT CATAACATAC TGTTTTTCT TACTCCACAC
5881 AGGCATAGAG TGTCTGCTAT TAATAACTAT GCTCAAAAAT TGTGTACCTT TAGCTTTTTA
5941 ATTTGTAAAG GGGTTAATAA GGAATATTTG ATGTATAGTG CCTTGACTAG AGATCATAAT
6001 CAGCCATACC ACATTTGTAG AGGTTTTACT TGCTTTAAAA AACCTCCCAC ACCTCCCCCT
6061 GAACCTGAAA CATAAAATGA ATGCAATTGT TGTTGTTAAC TTGTTTATTG CAGCTTATAA
```

FIG. 13B

```
6121 TGGTTACAAA TAAAGCAATA GCATCACAAA TTTCACAAAT AAAGCATTTT TTTCACTGCA
6181 TTCTAGTTGT GGTTTGTCCA AACTCATCAA TGTATCTTAT CATGTCTGGA TCGGCTGGAT
6241 GATCCTCCAG CGCGGGATC TCATGCTGGA GTTCTTCGCC CACCCCAACT TGTTTATTGC
6301 AGCTTATAAT GGTTACAAAT AAAGCAATAG CATCACAAAT TCACAAATA AAGCATTTT
6361 TTCACTGCAT TCTAGTTGTG GTTTGTCCAA ACTCATCAAT GTATCTTATC ATGTCTGTAT
6421 ACCGTCGACC TCTAGCTAGA GCTTGGCGTA ATCATGGTCA TAGCTGTTTC CTGTGTGAAA
6481 TTGTTATCCG CTCACAATTC CACACAACAT ACGAGCCGGA AGCATAAAGT GTAAAGCCTG
6541 GGGTGCCTAA TGAGTGAGCT AACTCACATT AATTGCGTTG CGCTCACTGC CCGCTTTCCA
6601 GTCGGGAAAC CTGTCGTGCC AGCTGCATTA ATGAATCGGC CAACGCGCGG GGAGAGGCGG
6661 TTTGCGTATT GGGCGCTCTT CCGCTTCCTC GCTCACTGAC TCGCTGCGCT CGGTCGTTCG
6721 GCTGCGGCGA GCGGTATCAG CTCACTCAAA GGCGGTAATA CGGTTATCCA CAGAATCAGG
6781 GGATAACGCA GGAAAGAACA TGTGAGCAAA AGGCCAGCAA AAGGCCAGGA ACCGTAAAAA
6841 GGCCGCGTTG CTGGCGTTTT TCCATAGGCT CCGCCCCCCT GACGAGCATC ACAAAAATCG
6901 ACGCTCAAGT CAGAGGTGGC GAAACCCGAC AGGACTATAA AGATACCAGG CGTTTCCCCC
6961 TGGAAGCTCC CTCGTGCGCT CTCCTGTTCC GACCCTGCCG CTTACCGGAT ACCTGTCCGC
7021 CTTTCTCCCT TCGGGAAGCG TGGCGCTTTC TCAATGCTCA CGCTGTAGGT ATCTCAGTTC
7081 GGTGTAGGTC GTTCGCTCCA AGCTGGGCTG TGTGCACGAA CCCCCGTTC AGCCCGACCG
7141 CTGCGCCTTA TCCGGTAACT ATCGTCTTGA GTCCAACCCG GTAAGACACG ACTTATCGCC
7201 ACTGGCAGCA GCCACTGGTA ACAGGATTAG CAGAGCGAGG TATGTAGGCG GTGCTACAGA
7261 GTTCTTGAAG TGGTGGCCTA ACTACGGCTA CACTAGAAGG ACAGTATTTG GTATCTGCGC
7321 TCTGCTGAAG CCAGTTACCT TCGGAAAAAG AGTTGGTAGC TCTTGATCCG GCAAACAAAC
7381 CACCGCTGGT AGCGGTGGTT TTTTGTTTG CAAGCAGCAG ATTACGCGCA GAAAAAAGG
7441 ATCTCAAGAA GATCCTTTGA TCTTTTCTAC GGGGTCTGAC GCTCAGTGGA ACGAAAACTC
7501 ACGTTAAGGG ATTTTGGTCA TGAGATTATC AAAAAGGATC TTCACCTAGA TCCTTTTAAA
7561 TTAAAAATGA AGTTTTAAAT CAATCTAAAG TATATATGAG TAAACTTGGT CTGACAGTTA
7621 CCAATGCTTA ATCAGTGAGG CACCTATCTC AGCGATCTGT CTATTTCGTT CATCCATAGT
7681 TGCCTGACTC CCCGTCGTGT AGATAACTAC GATACGGGAG GGCTTACCAT CTGGCCCCAG
7741 TGCTGCAATG ATACCGCGAG ACCCACGCTC ACCGGCTCCA GATTTATCAG CAATAAACCA
7801 GCCAGCCGGA AGGGCCGAGC GCAGAAGTGG TCCTGCAACT TTATCCGCCT CCATCCAGTC
7861 TATTAATTGT TGCCGGGAAG CTAGAGTAAG TAGTTCGCCA GTTAATAGTT TGCGCAACGT
7921 TGTTGCCATT GCTACAGGCA TCGTGGTGTC ACGCTCGTCG TTTGGTATGG CTTCATTCAG
7981 CTCCGGTTCC CAACGATCAA GGCGAGTTAC ATGATCCCCC ATGTTGTGCA AAAAAGCGGT
8041 TAGCTCCTTC GGTCCTCCGA TCGTTGTCAG AAGTAAGTTG GCCGCAGTGT TATCACTCAT
8101 GGTTATGGCA GCACTGCATA ATTCTCTTAC TGTCATGCCA TCCGTAAGAT GCTTTTCTGT
8161 GACTGGTGAG TACTCAACCA AGTCATTCTG AGAATAGTGT ATGCGGCGAC CGAGTTGCTC
8221 TTGCCCGGCG TCAATACGGG ATAATACCGC GCCACATAGC AGAACTTTAA AAGTGCTCAT
8281 CATTGGAAAA CGTTCTTCGG GGCGAAAACT CTCAAGGATC TTACCGCTGT TGAGATCCAG
8341 TTCGATGTAA CCCACTCGTG CACCCAACTG ATCTTCAGCA TCTTTTACTT TCACCAGCGT
8401 TTCTGGGTGA GCAAAAACAG GAAGGCAAAA TGCCGCAAAA AAGGGAATAA GGGCGACACG
8461 GAAATGTTGA ATACTCATAC TCTTCCTTTT TCAATATTAT TGAAGCATTT ATCAGGGTTA
8521 TTGTCTCATG AGCGGATACA TATTTGAATG TATTTAGAAA AATAAACAAA TAGGGGTTCC
8581 GCGCACATTT CCCCGAAAAG TGCCACCTGA CGTC
```

FIG. 13C

```
   1  GACGGATCGG GAGATCTGCT AGCCCGGGTG ACCTGAGGCG CGCCGGCTTC GAATAGCCAG
  61  AGTAACCTTT TTTTTTAATT TTATTTTATT TTATTTTTGA GATGGAGTTT GGCGCCGATC
 121  TCCCGATCCC CTATGGTCGA CTCTCAGTAC AATCTGCTCT GATGCCGCAT AGTTAAGCCA
 181  GTATCTGCTC CCTGCTTGTG TGTTGAGGT CGCTGAGTAG TGCGCGAGCA AAATTTAAGC
 241  TACAACAAGG CAAGGCTTGA CCGACAATTG CATGAAGAAT CTGCTTAGGG TTAGGCGTTT
 301  TGCGCTGCTT CGCGATGTAC GGGCCAGATA TACGCGTTGA CATTGATTAT TGACTAGTTA
 361  TTAATAGTAA TCAATTACGG GGTCATTAGT TCATAGCCCA TATATGGAGT TCCGCGTTAC
 421  ATAACTTACG GTAAATGGCC CGCCTGGCTG ACCGCCCAAC GACCCCGCC CATTGACGTC
 481  AATAATGACG TATGTTCCCA TAGTAACGCC AATAGGGACT TTCCATTGAC GTCAATGGGT
 541  GGACTATTTA CGGTAAACTG CCCACTTGGC AGTACATCAA GTGTATCATA TGCCAAGTAC
 601  GCCCCCTATT GACGTCAATG ACGGTAAATG GCCCGCCTGG CATTATGCCC AGTACATGAC
 661  CTTATGGGAC TTTCCTACTT GGCAGTACAT CTACGTATTA GTCATCGCTA TTACCATGGT
 721  GATGCGGTTT TGGCAGTACA TCAATGGGCG TGGATAGCGG TTTGACTCAC GGGGATTTCC
 781  AAGTCTCCAC CCCATTGACG TCAATGGGAG TTTGTTTTGG CACCAAAATC AACGGGACTT
 841  TCCAAAATGT CGTAACAACT CCGCCCCATT GACGCAAATG GCGGTAGGC GTGTACGGTG
 901  GGAGGTCTAT ATAAGCAGAG CTCTCTGGCT AACTAGAGAA CCCACTGCTT ACTGGCTTAT
 961  CGAAATTAAT ACGACTCACT ATAGGGAGAC CAAGCTTGG TACCATGGAA GCCCCAGCTC
1021  AGCTTCTCTT CCTCCTGCTA CTCTGGCTCC CAGATACCAC CGGAGACATT GTTCTGACTC
1081  AGTCTCCAGC CACCCTGTCT GTGACTCCAG GAGATAGAGT CTCTCTTTCC TGCAGGGCCA
1141  GCCAGAGTAT TAGCGACTAC TTACACTGGT ATCAACAAAA ATCACATGAG TCTCCAAGGC
1201  TTCTCATCAA ATATGCTTCC CATTCCATCT CTGGGATCCC CTCCAGGTTC AGTGGCAGTG
1261  GATCAGGGTC AGATTTCACT CTCAGTATCA ACAGTGTGGA ACCTGAAGAT GTTGGAATTT
1321  ATTACTGTCA ACATGGTCAC AGCTTTCCGT GGACGTTCGG TGGAGGCACC AAGCTGGAAA
1381  TCAAACGTAA GTCTCGAGTC TCTAGATAAC CGGTCAATCG GTCAATGATT GGAATTCTA
1441  AACTCTGAGG GGGTCGGATG ACGTGGCCAT TCTTTGCCTA AAGCATTGAG TTTACTGCAA
1501  GGTCAGAAAA GCATGCAAAG CCCTCAGAAT GGCTGCAAAG AGCTCCAACA AAACAATTTA
1561  GAACTTTATT AAGGAATAGG GGGAAGCTAG GAAGAAACTC AAAACATCAA GATTTTAAAT
1621  ACGCTTCTTG GTCTCCTTGC TATAATTATC TGGGATAAGC ATGCTGTTTT CTGTCTGTCC
1681  CTAACATGCC CTTATCCGCA AACAACACAC CCAAGGGCAG AACTTTGTTA CTTAAACACC
1741  ATCCTGTTTG CTTCTTTCCT CAGGAACTGT GGCTGCACCA TCTGTCTTCA TCTTCCCGCC
1801  ATCTGATGAG CAGTTGAAAT CTGGAACTGC CTCTGTTGTG TGCCTGCTGA ATAACTTCTA
1861  TCCCAGAGAG GCCAAAGTAC AGTGGAAGGT GGATAACGCC CTCCAATCGG GTAACTCCCA
1921  GGAGAGTGTC ACAGAGCAGG ACAGCAAGGA CAGCACCTAC AGCCTCAGCA GCACCCTGAC
1981  GCTGAGCAAA GCAGACTACG AGAAACACAA AGTCTACGCC TGCGAAGTCA CCCATCAGGG
2041  CCTGAGCTCG CCCGTCACAA AGAGCTTCAA CAGGGGAGAG TGTTAGAGGG AGAAGTGCCC
2101  CCACCTGCTC CTCAGTTCCA GCCTGACCCC CTCCCATCCT TTGGCCTCTG ACCCTTTTTC
2161  CACAGGGGAC CTACCCCTAT TGCGGTCCTC CAGCTCATCT TTCACCTCAC CCCCCCTCCTC
2221  CTCCTTGGCT TTAATTATGC TAATGTTGGA GGAGAATGAA TAAATAAAGT GAATCTTTGC
2281  ACCTGTGGTT TCTCTCTTTC CTCATTTAAT AATTATTATC TGTTGTTTTA CCAACTACTC
2341  AATTTCTCTT ATAAGGGACT AAATATGTAG TCATCCTAAG GCACGTAACC ATTTATAAAA
2401  ATCATCCTTC ATTCTATTTT ACCCTATCAT CCTCTGCAAG ACAGTCCTCC CTCAAACCCA
2461  CAAGCCTTCT GTCCTCACAG TCCCCTGGGC CATGGTAGGA GAGACTTGCT TCCTTGTTTT
2521  CCCCTCCTCA GCAAGCCCTC ATAGTCCTTT TAAGGGTGA CAGGTCTTAC AGTCATATAT
2581  CCTTTGATTC AATTCCCTGA GAATCAACCA AAGCAAATTT TCAAAAGAA GAAACCTGCT
2641  ATAAAGAGAA TCATTCATTG CAACATGATA TAAAATAACA ACACAATAAA AGCAATTAAA
2701  TAAACAAACA ATAGGGAAAT GTTTAAGTTC ATCATGGTAC TTAGACTTAA TGGAATGTCA
2761  TGCCTTATTT ACATTTTTAA ACAGGTACTG AGGGACTCCT GTCTGCCAAG GGCCGTATTG
2821  AGTACTTTCC ACAACCTAAT TTAATCCACA CTATACTGTG AGATTAAAAA CATTCATTAA
2881  AATGTTGCAA AGGTTCTATA AAGCTGAGAG ACAAATATAT TCTATAACTC AGCAATCCCA
2941  CTTCTAGATG ACTGAGTGTC CCCACCCACC AAAAAACTAT GCAAGAATGT TCAAAGCAGC
3001  TTTATTTACA AAAGCCAAAA ATTGGAAATA GCCCGATTGT CCAACAATAG AATGAGTTAT
```

FIG. 14A

```
3061 TAAACTGTGG TATGTTTATA CATTAGAATA CCCAATGAGG AGAATTAACA AGCTACAACT
3121 ATACCTACTC ACACAGATGA ATCTCATAAA AATAATGTTA CATAAGAGAA ACTCAATGCA
3181 AAAGATATGT TCTGTATGTT TTCATCCATA TAAAGTTCAA AACCAGGTAA AAATAAAGTT
3241 AGAAATTTGG ATGGAAATTA CTCTTAGCTG GGGGTGGGCG AGTTAGTGCC TGGGAGAAGA
3301 CAAGAAGGGG CTTCTGGGGT CTTGGTAATG TTCTGTTCCT CGTGTGGGGT TGTGCAGTTA
3361 TGATCTGTGC ACTGTTCTGT ATACACATTA TGCTTCAAAA TAACTTCACA TAAAGAACAT
3421 CTTATACCCA GTTAATAGAT AGAAGAGGAA TAAGTAATAG GTCAAGACCA ACGCAGCTGG
3481 TAAGTGGGGG CCTGGGATCA AATAGCTACC TGCCTAATCC TGCCCWCTTG AGCCCTGAAT
3541 GAGTCTGCCT TCCAGGGCTC AAGGTGCTCA ACAAAACAAC AGGCCTGCTA TTTTCCTGGC
3601 ATCTGTGCCC TGTTTGGCTA GCTAGGAGCA CACATACATA GAAATTAAAT GAAACAGACC
3661 TTCAGCAAGG GGACAGAGGA CAGAATTAAC CTTGCCCAGA CACTGGAAAC CCATGTATGA
3721 ACACTCACAT GTTTGGGAAG GGGGAAGGGC ACATGTAAAT GAGGACTCTT CCTCATTCTA
3781 TGGGGCACTC TGGCCCTGCC CCTCTCAGCT ACTCATCCAT CCAACACACC TTTCTAAGTA
3841 CCTCTCTCTG CCTACACTCT GAAGGGGTTC AGGAGTAACT AACACAGCAT CCCTTCCCTC
3901 AAATGACTGA CAATCCCTTT GTCCTGCTTT GTTTTTCTTT CCAGTCAGTA CTGGGAAAGT
3961 GGGGAAGGAC AGTCATGGAG AAACTACATA AGGAAGCACC TTGCCCTTCT GCCTCTTGAG
4021 AATGTTGATG AGTATCAAAT CTTTCAAACT TTGGAGGTTT GAGTAGGGGT GAGACTCAGT
4081 AATGTCCCTT CCAATGACAT GAACTTGCTC ACTCATCCCT GGGGGCCAAA TTGAACAATC
4141 AAAGGCAGGC ATAATCCAGT TATGAATTCT TGCGGCCGCT TGCTAGCTTC ACGTGTTGGA
4201 TCCAACCGCG GAAGGGCCCT ATTCTATAGT GTCACCTAAA TGCTAGAGCT CGCTGATCAG
4261 CCTCGACTGT GCCTTCTAGT TGCCAGCCAT CTGTTGTTTG CCCCTCCCCC GTGCCTTCCT
4321 TGACCCTGGA AGGTGCCACT CCCACTGTCC TTTCCTAATA AAATGAGGAA ATTGCATCGC
4381 ATTGTCTGAG TAGGTGTCAT TCTATTCTGG GGGTGGGGT GGGGCAGGAC AGCAAGGGGG
4441 AGGATTGGGA AGACAATAGC AGGCATGCTG GGGATGCGGT GGGCTCTATG GCTTCTGAGG
4501 CGGAAAGAAC CAGCTGGGGC TCTAGGGGT ATCCCCACGC GCCCTGTAGC GGCGCATTAA
4561 GCGCGGCGGG TGTGGTGGTT ACGCGCAGCG TGACCGCTAC ACTTGCCAGC GCCCTAGCGC
4621 CCGCTCCTTT CGCTTTCTTC CCTTCCTTTC TCGCCACGTT CGCCGGGCCT CTCAAAAAAG
4681 GGAAAAAAAG CATGCATCTC AATTAGTCAG CAACCATAGT CCCGCCCCTA ACTCCGCCCA
4741 TCCCGCCCCT AACTCCGCCC AGTTCCGCCC ATTCTCCGCC CCATGGCTGA CTAATTTTTT
4801 TTATTTATGC AGAGGCCGAG GCCGCCTCGG CCTCTGAGCT ATTCCAGAAG TAGTGAGGAG
4861 GCTTTTTTGG AGGCCTAGGC TTTTGCAAAA AGCTTGGACA GCTCAGGGCT GCGATTTCGC
4921 GCCAAACTTG ACGGCAATCC TAGCGTGAAG GCTGGTAGGA TTTTATCCCC GCTGCCATCA
4981 TGGTTCGACC ATTGAACTGC ATCGTCGCCG TGTCCCAAAA TATGGGGATT GGCAAGAACG
5041 GAGACCTACC CTGGCCTCCG CTCAGGAACG AGTTCAAGTA CTTCCAAAGA ATGACCACAA
5101 CCTCTTCAGT GGAAGGTAAA CAGAATCTGG TGATTATGGG TAGGAAAACC TGGTTCTCCA
5161 TTCCTGAGAA GAATCGACCT TTAAAGGACA GAATTAATAT AGTTCTCAGT AGAGAACTCA
5221 AGAACCACC ACGAGGAGCT CATTTTCTTG CCAAAAGTTT GGATGATGCC TTAAGACTTA
5281 TTGAACAACC GGAATTGGCA AGTAAAGTAG ACATGGTTTG GATAGTCGGA GGCAGTTCTG
5341 TTTACCAGGA AGCCATGAAT CAACCAGGCC ACCTTAGACT CTTTGTGACA AGGATCATGC
5401 AGGAATTTGA AAGTGACACG TTTTTCCCAG AAATTGATTT GGGGAAATAT AAACTTCTCC
5461 CAGAATACCC AGGCGTCCTC TCTGAGGTCC AGGAGGAAAA AGGCATCAAG TATAAGTTTG
5521 AAGTCTACGA GAAGAAAGAC TAACAGGAAG ATGCTTTCAA GTTCTCTGCT CCCCTCCTAA
5581 AGCTATGCAT TTTTATAAGA CCATGGGACT TTTGCTGGCT TTAGATCTCT TTGTGAAGGA
5641 ACCTTACTTC TGTGGTGTGA CATAATTGGA CAAACTACCT ACAGAGATTT AAAGCTCTAA
5701 GGTAAATATA AAATTTTTAA GTGTATAATG TGTTAAACTA CTGATTCTAA TTGTTTGTGT
5761 ATTTTAGATT CCAACCTATG GAACTGATGA ATGGGAGCAG TGGTGGAATG CCTTTAATGA
5821 GGAAAACCTG TTTTGCTCAG AAGAAATGCC ATCTAGTGAT GATGAGGCTA CTGCTGACTC
5881 TCAACATTCT ACTCCTCCAA AAAGAAGAG AAAGGTAGAA GACCCCAAGG ACTTTCCTTC
5941 AGAATTGCTA AGTTTTTTGA GTCATGCTGT GTTTAGTAAT AGAACTCTTG CTTGCTTTGC
6001 TATTTACACC ACAAAGGAAA AAGCTGCACT GCTATACAAG AAAATTATGG AAAAATATTC
6061 TGTAACCTTT ATAAGTAGGC ATAACAGTTA TAATCATAAC ATACTGTTTT TTCTTACTCC
```

FIG. 14B

```
6121 ACACAGGCAT AGAGTGTCTG CTATTAATAA CTATGCTCAA AAATTGTGTA CCTTTAGCTT
6181 TTTAATTTGT AAAGGGGTTA ATAAGGAATA TTTGATGTAT AGTGCCTTGA CTAGAGATCA
6241 TAATCAGCCA TACCACATTT GTAGAGGTTT TACTTGCTTT AAAAAACCTC CCACACCTCC
6301 CCCTGAACCT GAAACATAAA ATGAATGCAA TTGTTGTTGT TAACTTGTTT ATTGCAGCTT
6361 ATAATGGTTA CAAATAAAGC AATAGCATCA CAAATTTCAC AAATAAAGCA TTTTTTTCAC
6421 TGCATTCTAG TTGTGGTTTG TCCAAACTCA TCAATGTATC TTATCATGTC TGGATCGGCT
6481 GGATGATCCT CCAGCGCGGG GATCTCATGC TGGAGTTCTT CGCCCACCCC AACTTGTTTA
6541 TTGCAGCTTA TAATGGTTAC AAATAAAGCA ATAGCATCAC AAATTTCACA AATAAAGCAT
6601 TTTTTTCACT GCATTCTAGT TGTGGTTTGT CCAAACTCAT CAATGTATCT TATCATGTCT
6661 GTATACCGTC GACCTCTAGC TAGAGCTTGG CGTAATCATG GTCATAGCTG TTTCCTGTGT
6721 GAAATTGTTA TCCGCTCACA ATTCCACACA ACATACGAGC CGGAAGCATA AAGTGTAAAG
6781 CCTGGGGTGC CTAATGAGTG AGCTAACTCA CATTAATTGC GTTGCGCTCA CTGCCCGCTT
6841 TCCAGTCGGG AAACCTGTCG TGCCAGCTGC ATTAATGAAT CGGCCAACGC GCGGGGAGAG
6901 GCGGTTTGCG TATTGGGCGC TCTTCCGCTT CCTCGCTCAC TGACTCGCTG CGCTCGGTCG
6961 TTCGGCTGCG GCGAGCGGTA TCAGCTCACT CAAAGGCGGT AATACGGTTA TCCACAGAAT
7021 CAGGGGATAA CGCAGGAAAG AACATGTGAG CAAAAGGCCA GCAAAAGGCC AGGAACCGTA
7081 AAAAGGCCGC GTTGCTGGCG TTTTTCCATA GGCTCCGCCC CCTGACGAG CATCACAAAA
7141 ATCGACGCTC AAGTCAGAGG TGGCGAAACC CGACAGGACT ATAAAGATAC CAGGCGTTTC
7201 CCCCTGGAAG CTCCCTCGTG CGCTCTCCTG TTCCGACCCT GCCGCTTACC GGATACCTGT
7261 CCGCCTTTCT CCCTTCGGGA AGCGTGGCGC TTTCTCAATG CTCACGCTGT AGGTATCTCA
7321 GTTCGGTGTA GGTCGTTCGC TCCAAGCTGG GCTGTGTGCA CGAACCCCCC GTTCAGCCCG
7381 ACCGCTGCGC CTTATCCGGT AACTATCGTC TTGAGTCCAA CCCGGTAAGA CACGACTTAT
7441 CGCCACTGGC AGCAGCCACT GGTAACAGGA TTAGCAGAGC GAGGTATGTA GGCGGTGCTA
7501 CAGAGTTCTT GAAGTGGTGG CCTAACTACG GCTACACTAG AAGGACAGTA TTTGGTATCT
7561 GCGCTCTGCT GAAGCCAGTT ACCTTCGGAA AAAGAGTTGG TAGCTCTTGA TCCGGCAAAC
7621 AAACCACCGC TGGTAGCGGT GGTTTTTTTG TTTGCAAGCA GCAGATTACG CGCAGAAAAA
7681 AAGGATCTCA AGAAGATCCT TTGATCTTTT CTACGGGGTC TGACGCTCAG TGGAACGAAA
7741 ACTCACGTTA AGGGATTTTG GTCATGAGAT TATCAAAAAG GATCTTCACC TAGATCCTTT
7801 TAAATTAAAA ATGAAGTTTT AAATCAATCT AAAGTATATA TGAGTAAACT TGGTCTGACA
7861 GTTACCAATG CTTAATCAGT GAGGCACCTA TCTCAGCGAT CTGTCTATTT CGTTCATCCA
7921 TAGTTGCCTG ACTCCCCGTC GTGTAGATAA CTACGATACG GGAGGGCTTA CCATCTGGCC
7981 CCAGTGCTGC AATGATACCG CGAGACCCAC GCTCACCGGC TCCAGATTTA TCAGCAATAA
8041 ACCAGCCAGC CGGAAGGGCC GAGCGCAGAA GTGGTCCTGC AACTTTATCC GCCTCCATCC
8101 AGTCTATTAA TTGTTGCCGG GAAGCTAGAG TAAGTAGTTC GCCAGTTAAT AGTTTGCGCA
8161 ACGTTGTTGC CATTGCTACA GGCATCGTGG TGTCACGCTC GTCGTTTGGT ATGGCTTCAT
8221 TCAGCTCCGG TTCCCAACGA TCAAGGCGAG TTACATGATC CCCCATGTTG TGCAAAAAAG
8281 CGGTTAGCTC CTTCGGTCCT CCGATCGTTG TCAGAAGTAA GTTGGCCGCA GTGTTATCAC
8341 TCATGGTTAT GGCAGCACTG CATAATTCTC TTACTGTCAT GCCATCCGTA AGATGCTTTT
8401 CTGTGACTGG TGAGTACTCA ACCAAGTCAT TCTGAGAATA GTGTATGCGG CGACCGAGTT
8461 GCTCTTGCCC GGCGTCAATA CGGGATAATA CCGCGCCACA TAGCAGAACT TTAAAAGTGC
8521 TCATCATTGG AAAACGTTCT TCGGGGCGAA AACTCTCAAG GATCTTACCG CTGTTGAGAT
8581 CCAGTTCGAT GTAACCCACT CGTGCACCCA ACTGATCTTC AGCATCTTTT ACTTTCACCA
8641 GCGTTTCTGG GTGAGCAAAA ACAGGAAGGC AAAATGCCGC AAAAAAGGGA ATAAGGGCGA
8701 CACGGAAATG TTGAATACTC ATACTCTTCC TTTTTCAATA TTATTGAAGC ATTTATCAGG
8761 GTTATTGTCT CATGAGCGGA TACATATTTG AATGTATTTA GAAAAATAAA CAAATAGGGG
8821 TTCCGCGCAC ATTTCCCCGA AAAGTGCCAC CTGACGTC
```

FIG. 14C

METHODS OF USING ANTIBODIES AGAINST HUMAN CD40

This application is a divisional application of U.S. Ser. No. 09/026,291, filed Feb. 19, 1998, now U.S. Pat. No. 6,051,228.

BACKGROUND OF THE INVENTION

Immune/inflammatory responses are mediated by a complex series of interactions. One receptor/ligand pair shown to be important in these processes is CD40/gp39. The gp39/CD40 interaction mediates a number of important signaling events between activated T cells and other effect or cells of the immune system leading to amplification of an immune/inflammatory response. Responses to signaling through CD40 include T cell help to B cells in the humoral immune response, induction of cytokines by monocytes, and expression of adhesion molecules by endothelial cells.

CD40 is a type I cell surface receptor and a member of the tumor necrosis factor receptor (TNFR) supergene family. Though originally identified as a B cell antigen, CD40 is now believed to be expressed by all antigen presenting cells (APC), including dendritic cells, keratinocytes, and monocytes. CD40 is also expressed by cell types that can act as APC under certain conditions, such as vascular endothelial cells, or cells involved in direct interactions with T cells or T cell precursors such as thymic epithelial cells. More recently, it has also been reported that CD40 can be expressed by fibroblasts, eosinophils, and activated T cells. CD40 expression has also been seen in cancerous cells. Evidence for this is primarily derived from the identification of some carcinoma and melanoma derived cell lines which are $CD40^+$. (Clark and Ledbetter, *Proc. Natl. Acad. Sci.* (1986) 83:4494–98; Schriever et al., *J. Exp. Med.* (1989) 169:2043–58; Caux et al., *J. Exp. Med.* (1994) 180:1263–72; Alderson et al., *J. Exp. Med.* (1993) 178:669–74; Young et al., *Int. J. Cancer* (1989) 43:786–94; Paulie et al., *Cancer Immunol. Immunother.* (1985) 20:23–28; Denfeld et al., *Eur. J. Immunol.* (1996) 26:2329–34; Gaspari et al., *Eur. J. Immunol.* (1996) 26:1371–77; Peguet-Navarro et al., *J. Immunol.* (1997) 158:144–52; Hollenbaugh et al., *J. Exp. Med.* (1995) 182:3340; Galy and Spits, *J. Immunol.* (1992) 149:775–82; Yellin et al., *J. Leukoc. Biol.* (1995) 58:209–16; Ohkawara et al., *J. Clin. Invest.* (1996) 97:176146).

This expression pattern differs from the expression pattern of the Ligand of CD40, namely gp39. A member of the tumor necrosis factor (TNF) family of proteins, gp39 is a type II cell surface protein that is transiently expressed by activated T cells. Gp39 is also known as CD40L, TRAP, T-BAM, and now has the official CD designation from the Leukocyte Workshop of CD154. In in vitro assays, gp39 appears on the T cells approximately 2–4 hours following T cell activation and levels peak at 6–8 hours. The protein level then rapidly declines and is undetectable 24 hours after stimulation. Gp39 expression has also been detected on eosinophils and mast cells. (Noelle et al., *Proc. Natl Acad. Sci.* (1992) 89:6550–54; Hollenbaugh et al., *EMBO J.* (1992) 11:4313–21; Spriggs et al., *J. Exp. Med.* (1992) 176:1543–50; Graf et al., *Eur. J. Immunol.* (1992) 22:3191–94; Covey et al., *Mol. Immunol.* (1994) 31:471–84; Castle et al., *J. Immunol.* (1993) 151:1777–88; Roy et al., *J. Immunol.* (1993) 151:2497–2510; Gauchat et al., *Nature* (1993) 365:34043; Gauchat et al., *Eur. J. Immunol.* (1995) 25:863–65; Koshy et al., *J. Clin. Invest.* (1996) 98:826–37; Desai-Mehta et al., *J. Clin. Invest.* (1996) 97:2063–73).

CD40 is a potent signaling receptor, providing a mechanism for activated T-cells to regulate a wide range of immune and inflammatory responses. In vitro and in vivo studies with recombinant forms of the gp39 ligand and with anti-CD40 mAbs have shown that signaling through this receptor leads to a cellular response in all known $CD40^+$ cells, and that outcome not only varies by cell type but is also modulated by concurrent signaling events through other receptors. In B cells, for example, CD40 signaling in conjunction with signaling by the IL-4 receptor leads to B cell proliferation and production of antibodies of the IgE isotype, while CD40 signaling in conjunction with signals from the IL-10 receptor lead to B cell proliferation and production of antibodies of the IgG isotype (Gordon et al., *Eur. J Immunol.* (1987) 17:1535–38; Rousset et al., *J. Exp. Med.* (1991) 173:705–710; Jabara et al., *J. Exp. Med.* (1990) 172:1861–64; Gascan et al., *J. Immunol.* (1991) 147:8–13). Gp39 mediated CD40 signaling may play a role in cellular immunity through the induction of CD80 and CD86, important T cell costimulatory molecules which bind CD28 and CTLA4 (Goldstein et al., *Mol. Immunol.* (1996) 33:541–52).

The CD40/gp39 receptor/ligand system is one of the many systems which are involved in the productive interaction between activated T cells and other cells of the immune system. However, a number of findings suggest that this interaction is unique and central to the regulation of the humoral immune response in humans. In particular, defects in gp39 expression or structure have been shown to be the cause of the human immunodeficiency known as X-linked hyper IgM (X-HIM) syndrome. This immunodeficiency is characterized by the inability of affected individuals to produce antibodies other than those of the IgM isotype, indicating that the productive interaction between gp39 and CD40 is required for an effective humoral immune response (Allen et al., *Science* (1993) 259:990–93; Aruffo et al., *Cell* (1993) 72:291–300; Di Santo et al., *Nature* (1993) 361:541–43; Fuleihan, et al., *Proc. Natl. Acad. Sci.* (1993) 90(6):2170–73; Korthauer et al., *Nature* (1993) 361:539–541; Notarangelo et al., *Immunodef. Rev.* (1992) 3:101–22). Likewise, recent data indicate that non-X-linked HIM syndrome in humans is caused by defects in the CD40 molecule. Using gene knockout technology, mice lacking CD40 or gp39 have been generated. These mice exhibit a phenotype which has the same characteristics as HIM syndrome suggesting that mice can be an appropriate model in which to test the effects of in vivo treatment with either anti-CD40 or anti-gp39 mAbs that block the interaction between CD40 and gp39 (Kawabe et al., *Immunity* (1994) 1:167–78; Xu et al., *Immunity* (1994) 1:423–431; Renshaw et al., *J. Exp. Med.* (1 994) 180:1889–1900; Castigli et al., *Proc. Natl. Acad. Sci. USA* (1994) 91:12135–39).

The effects of in vivo inhibition of the CD40/gp39 interaction have been extensively studied in normal mice and mouse models of disease using a hamster anti-mouse gp39 mAb (MR1). The immunosuppressive capacity of the antibody is reflected in its ability to completely inhibit the humoral immune response to T-cell dependent antigens (Foy, et al., *J. Exp. Med.* (1993) 178:1567–75). Several mouse models of immune diseases have also been shown to be inhibited by treatment with the antibody, including those mediated by cellular immune responses. Disease models shown to be inhibited by treatment with anti-gp39 include collagen induced arthritis, experimental allergic encephalomyelitis, lupus nephritis, transplant rejection, and graft vs. host disease (Durie et al., *Science* (1993) 261:1328–30; Berry, et al., unpublished; Gerritse et al., *Proc. Natl. Acad. Sci. USA* (1995) 93:2499–504; Mohan et al., *J. Immunol.* (1995) 154:1470–1480; Larsen et al., Transplantation (1996) 61:4–9; Hancock et al., *Proc. Natl. Acad.*

Sci. USA (1996) 93:13967–12; Parker et al., *Proc. Natl. Acad. Sci. USA* (1995) 92:9560–64; Durie, et al., *J. Clin. Invest.* (1994) 94:1333–38; Wallace, et al., unpublished). The role of CD40/gp39 in the amplification of a cellular immune response may be direct, through the stimulation of a subset of activated T cells that are capable of expressing CD40, or indirect, through induction of cytokines and the expression of important co-stimulatory cell surface molecules such as CD80 and CD86, which bind to the T cell receptors CD28 and CTLA-4. The anti-inflammatory effects of the inhibitor have been demonstrated by studies in a mouse model of oxygen-induced lung injury. The effects on inflammation in vivo are suggested by the in vitro results demonstrating stimulation of CD40 on vascular endothelial cells and monocytes which results in the expression of cell adhesion molecules, nitric oxide (NO), matrix metalloproteinases and proinflammatory cytokines (Kiener et al, *J. Immunol.* (1995) 155:4917–25; Malik et al., *J. Immunol.* (1995) 156:3952–60; Hollenbaugh et al., *J. Exp. Med.* (1995) 182:33–40).

Studies with anti-human gp39 mAbs in monkeys have shown that biologics which inhibit the interaction between gp39 and CD40 in vivo are effective immunosuppressive agents in primates. Anti-gp39 mAbs have been demonstrated to be effective in the inhibition of antibody responses to T-cell dependent antigens, and to protect allografts from rejection, results analogous to that seen in rodents.

Collectively the above studies have shown that agents which disrupt the interaction between gp39 and CD40 would be potent immunosuppressive and anti-inflammatory agents. Therefore, there exists a need in the art for an effective method of blocking the CD40/gp39 interaction to provide an immunosuppressive or anti-inflammatory effect. A purpose of the present invention is to provide an antibody which blocks the interaction between gp39 and CD40.

Another object of the present invention is to provide a chimeric antibody effective in blocking the interaction between CD40 and gp39.

An additional object of the present invention is to provide a humanized antibody effective in blocking the interaction between CD40 and gp39.

A further object of the present invention is a method of modulating an immune response by administering an antibody, chimeric antibody, or humanized antibody of the present invention. The method may be useful in treating any number of auto immune diseases, as well as skin or other organ transplantation.

SUMMARY OF THE INVENTION

The present invention comprises a novel antibody, more preferably a chimerized anti-human CD40 monoclonal antibody (mAb), which blocks the interaction between gp39 and CD40. In one embodiment of the present invention, a particularly preferred chimerized anti-human CD40 mAb is referred to as "chi220". Chi220 is a chimeric antibody comprising murine variable and human kappa and gamma 1 constant regions. Chi220, like its parent mouse mAb, binds to CD40 and, as a result, effectively blocks humoral immune responses to T cell-dependent antigens in a dose dependent fashion.

The anti-CD40 antibodies of the present invention, preferably chi220, are effective in modulating humoral immune responses against T cell-dependent antigens, collagen induced arthritis, and transplant rejection. The anti-CD40 antibodies of the present invention, preferably chi220, are also useful for their anti-inflammatory properties (which are similar to those seen with anti-gp39).

The antibodies of the present invention, particularly the anti-CD40 chimeric antibody chi220, have wide therapeutic applications, including auto immune diseases, inflammatory diseases and transplantation. Because of the expression of CD40 seen on malignant cells of several histologic types, the potential oncology applications of anti-CD40 antibodies, particularly the chi220 antibody of the present invention, are evident.

The following abbreviations are used throughout the present application and are known by those skilled in the art: APC (antigen presenting cell); CHO (chinese hamster ovary); CIA (collagen-induced arthritis); Cmax (maximum serum concentration); COS (African green monkey fibroblast cell line); DMARD (disease modifying anti-rheumatic drugs); ELISA (enzyme-linked immunosorbent assay); EPT (end point titers); EU (endotoxin units); FITC (fluoroisothiocyanate); h106-2 (humanized anti-gp39 mAb); HAMA (human-anti-mouse antibodies); im (intramuscular); KLH (keyhole limpet hemocyanin); mAb (monoclonal antibody); MTX (methotrexate); OVA (ovalbunin); PBS (phosphate buffered saline); PCR (polymerase chain reaction); PE (phycoerytherin); sc (subcutaneous); SDS-PAGE (sodium dodecyl sulfate polyacrylamide gel electrophoresis); SEC (size exclusion chromatography); SRBC (sheep red blood cells); STR (stirred tank reactor); TNF (tumor necrosis factor); VL (antibody light chain variable region); VH (antibody heavy chain variable region).

The references cited in this application are herein incorporated by reference in their entirety.

BRIEF DESCRIPTION OF THE DRAWINGS

FIG. 3 shows the anti-SRBC antibody response in primates. FIG. 3a shows the results of analysis for IgM anti-SRBC antibodies. FIG. 3b shows the results of analysis for IgG anti-SRBC antibodies.

FIG. 4a shows the sequence of the light chain variable region of chi220 in bold (SEQ ID NO:1), and FIG. 4b shows the sequence of the heavy chain variable region of chi220 in bold (SEQ ID NO:2). The underlined sequences in FIG. 4a and 4b are the inserted signal sequences of the human antibody with the closest homology which had been used as humanization template.

FIG. 5 shows the results of in vitro assays testing chimeric and humanized antibody of the present invention.

FIG. 6 shows the IgM Anti-SRBC antibody response. FIG. 6a shows the results from monkeys that received 10, 40 or 100 mg/kg chi220. FIG. 6b shows the results from monkeys that received 0.1 or 1 mg/kg chi220.

FIG. 7 shows the IgG Anti-SRBC antibody response.

FIG. 8 shows the anti-OVA antibody response in primates.

FIG. 9 shows the anti-KLH antibody response in primates.

FIG. 13 provides a nucleic acid sequence (SEQ ID NO: 5) for an expression vector capable of expressing a heavy chain of a chimeric antibody of the present invention. The start ATG (nucleotides 1000–1002), encoding the start Met of the inserted signal sequence of the human antibody, is in bold. Nucleotides 1057 through 1422 SEQ ID NO: 7 underlined, provide a preferred nucleic acid sequence encoding a variable heavy chain of an antibody of the present invention.

FIG. 14 provides a nucleic acid sequence (SEQ ID NO: 7) for an expression vector capable of expressing a light chain of a chimeric antibody of the present invention. The start ATG (nucleotides 1005–1007), encoding the start Met of the inserted signal sequence of the human antibody, is in bold. Nucleotides 1065 through 1388 SEQ ID NO: 8 underlined, provide a preferred nucleic acid sequence encoding a variable light chain of an antibody of the present invention.

DETAILED DESCRIPTION OF THE INVENTION

Figure 1:
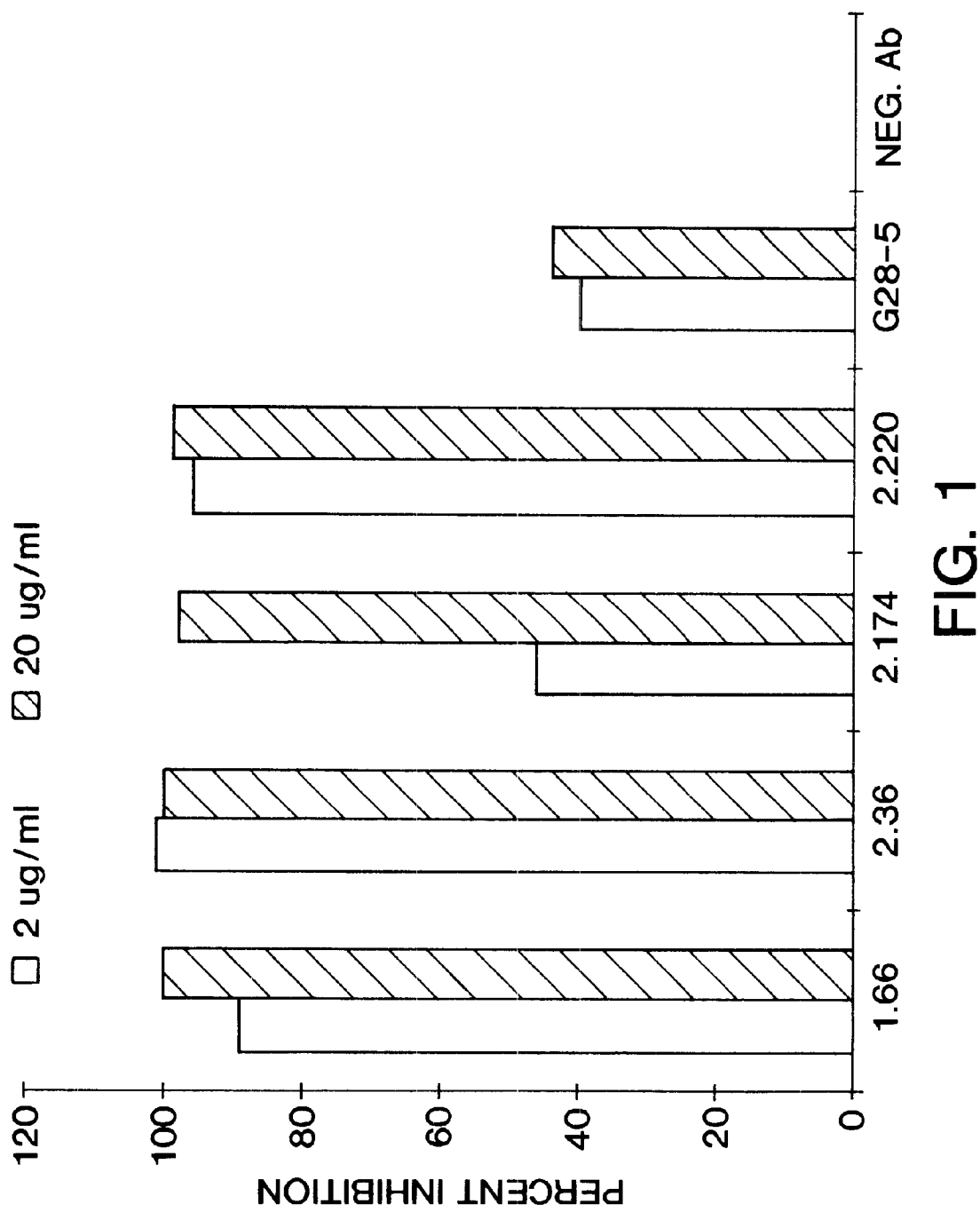
FIG. 1 shows the inhibition of sgp39 binding to Raji cells by anti-human CD40 mAbs.

The present inventors have developed an anti-human CD40 mAb with immunosuppressive properties. Such an anti-human CD40 mAb has obvious applications as a therapeutic. The present inventors have also developed a closely matched anti-mouse CD40 mAb (closely matched to the anti-human CD40 mAb) which is useful to study the effects of anti-CD40 mAb therapy in a number of mouse models of immune and inflammatory disease. Development of anti-CD40 antibodies is complicated by the fact that CD40 is a potent signaling molecule. Antibodies that bind to this antigen can be categorized based on the ability to stimulate CD40 signaling as well as the ability to block the CD40/gp39 interaction.

Applicants' anti-human CD40 mAb, which blocks the CD40/gp39 interaction, was selected from an extensive panel of anti-CD40 mAbs. The antibody, labeled 2.220, was chimerized. "Chimeric" antibodies comprise a light chain and a heavy chain: the light chain is comprised of a light chain variable region and a light chain constant region; the heavy chain is comprised of a heavy chain variable region and a heavy chain constant region. Chimeric antibodies comprise variable regions from one species and constant regions from another species (for example, mouse variable regions joined to human constant regions). (See, e.g., U.S. Pat. Nos. 4,816,397 and 4,816,567). Each of the light chain variable region (VL) and heavy chain variable region (VH) consists of "framework" regions interrupted by three hypervariable regions called "complementarity determining regions" or "CDRs". "Humanized" antibodies comprise antibodies with human framework regions combined with CDRs from a donor mouse or rat immunoglobulin. (See, e.g., U.S. Pat. No. 5,530,101) Also within the scope of the present invention are humanized antibodies which comprise CDRs derived from the murine variable chains disclosed herein.

Applicants' chimeric anti-CD40 antibody of the present invention is referred to herein as "chi220". Applicants' closely matched anti-mouse CD40 mAb is referred to herein as "7E1". Two different isotype variants of 7E1 were generated. These two variants of 7E1 are useful in examining the role of the Fc portion of the molecule in anti-CD40 mAb therapy in preclinical models of immune and inflammatory diseases. The generation of the anti-mouse CD46 mAb, the criteria used to select one which matched the properties of chi220, the generation of the isotype variants of the mAb and their in vivo activity in mouse models of immnune disease are also presented herein. Studies with both chi220 and its parent murine mAb 2.220 in monkeys, as well as studies with 7E1 in mice, showed that these anti-CD40 mAbs are potent immunosuppressive agents, and will be discussed in more detail below. The studies described herein were performed using standard technology known by those skilled in the art.

In summary, Applicants' chimeric anti-human CD40 mAb, and its parent mouse mAb, have been shown to suppress a humoral immune response in monkeys. Likewise, two isotype variants of a closely matched anti-mouse CD40 mAb, 7E1, showed immunosuppressive activity in a number of preclinical models of human disease. Taken together, these findings indicate that chi220 is useful for clinical application in the treatment of auto immune diseases and transplantation.

The following examples are for illustrative purposes only and do not limit the scope of Applicants invention, which is defined only by the claims.

EXAMPLE 1

Selection of Murine Anti-Human CD40 Antibody

A. Isolation and In Vitro Characterization

A panel of monoclonal antibodies was generated against human CD40 using standard hybridoma technology with human CD40 fusion protein as the immunogen. Antibodies were screened for binding to CD40 using both a CD40$^+$ cell line and fusion proteins. Assays of gp39 binding to CD40 and functional assays of stimulation through CD40 were used to characterize cloned antibodies. Selected antibodies were then characterized for crossreactivity with primate cells to assess the suitability of the antibodies for use in primate preclinical models.

1. Immunization and Fusion

Two fusions were performed to generate hybridomas producing anti-human CD40 mAbs. Immunizations to generate immune lymphocytes were carried out in 6–8 week old female BALB/c mice using as the immunogen a recombinant fusion protein consisting of the extracellular domain of human CD40 fused to the hinge, CH2 and CH3 domains of a murine IgG2b antibody (hCD40-mG2b).

For fusion 40-1, the mouse was initially immunized subcutaneously at 3–4 sites with an emulsion (total of 200 ul) of 30 ug hCD40-mG2b in complete Freund's adjuvant. The animal was similarly boosted on day 21 with hCD40-mG2b in incomplete Freund's adjuvant and then given a final pre-fusion immunization on day 37 by intravenous injection of 30 ug of hCD40-mG2b in PBS. Immunizations for fusion 40-2 were similarly performed except that Ribi adjuvant (R-730), universal Biologicals Ltd was substituted for Freund's adjuvant. Booster immunizations were on days 21 and 42 with the final pre-fusion boost on day 58.

Three days following final booster injections, leukocytes from the spleen and lymph nodes were harvested and fused at a 3:1 ratio with X63-Ag8.653 mouse myeloma cells using standard methods (Kearney et al., *J. Immunol.* (1979) 123:1548–50; Lane, *J. Immunol.* (1985) 81:223–28). Cell suspensions from each fusion were seeded into ten 96-well cell culture plates at a plating density of approximately 170,000 total cells (pre-fusion) per well.

2. Screening and Cloning

Two assay formats were used to identify mAbs with specificity for native human CD40. Cell culture supernatant from all wells were initially screened for their ability to bind to a CD40 positive, EBV-transformed human B cell line (1A2–2C) in an ELISA-based format. Each supernatant was then tested in an ELISA based format for reactivity with a purified, recombinant fusion protein consisting of the extracellular domain of human CD40 fused to the hinge, CH2 and CH3 domains of a human IgG1 antibody, hCD40-Ig, and a similarly constructed irrelevant human Ig fusion protein, Leu8-hIg (Hollenbaugh, et al., *EMBO J.* (1992) 11:4313–4321). Reactivity with the former and not the latter fusion protein, coupled with the cell binding data, established the presence of antibody specific for native CD40 in approximately 200 master wells.

A key functional property for the desired anti-CD40 mAb was the capacity to completely block the interaction of CD40 and its ligand, gp39. Thus, as the next step in antibody selection, all CD40 specific master well supernatants were assessed for their ability to inhibit the binding of the soluble, recombinant murine CD8-human gp39 fusion protein, sgp39, to immobilized hCD40-Ig in an ELISA-based format. Those that completely inhibited this interaction were subsequently titrated in the same format to establish which wells contained the highest titer of inhibiting antibody. From this analysis, ten of the most strongly inhibiting master wells were selected for cloning.

Cloning of the appropriate antibody secreting cells was accomplished in a two step process. Cells from each master well were first "minicloned" at a seeding density of 10 cells/well after which the highest titered, CD40-specific "miniclone" well was formally cloned by a limiting dilution method.

3. Further Characterization

Six assay formats were used to further characterize the antibodies. These were inhibition of sgp39 binding to human B cells, inhibition of B cell proliferation induced by sgp39 plus anti-IgM, inhibition of in vitro antibody synthesis by B cells induced by activated T cells, direct costimulation of B cells with anti-IgM, costimulation of B cells with anti-IgM in the presence of cross-linking anti-kappa light chain antibody, and costimulation of B cells with anti-IgM in the presence of a second anti-CD40 mAb, G28-5. This mAb was known to possess strong costimulatory activity and to incompletely block CD40/gp39 interaction. It has been included for comparison purposes in many of these assays.

This analysis led to the selection of four mAbs: 1.66 (IgG2b), 2.36 (IgG2a), 2.174 (IgG1) and 2.220 (IgG2a). Tests were run to characterize the mAbs. In one experiment, cells from the human B cell line Raji were incubated with 2 or 20 µg/ml of various anti-CD40 mAbs followed by a second incubation in undiluted COS cell supernatant containing mCD8-gp39 fusion protein (sgp39). Bound sgp39 was detected by further incubation of the cells with a FITC labeled anti-mCD8 mAb and analysis of the cells on a FACScan flow cut meter (Beaton Dickinson). Percent inhibition was calculated by dividing mean fluorescence of samples incubated with antibody by the mean fluorescence of samples without antibody in the first incubation (FIG. 1).

As shown in FIG. 1, each of these four mAbs was capable of completely inhibiting the binding of sgp39 fusion protein to a human B cell line expressing high levels of CD40, although in the case of 2.174, a relatively high concentration of antibody was required for complete blockade. Similar data were obtained using human tonsillar B cells. These data were paralleled by two functional assays. First, it was shown that each mAb was able to completely block sgp39-mediated costimulation of human tonsillar B cells. Second, each significantly inhibited the production of IgG and IgM in an in vitro T cell-dependent B cell antibody synthesis assay.

Three of the four antibodies showed limited ability to costimulate B cell proliferation in the presence of anti-IgM. MAb 2.220 was more consistent in its ability to induce weak costimulatory activity. With the addition of an anti-kappa light chain antibody, used to cross-link the anti-CD40 mAbs, 2.36 gained significant costimulatory activity, while the activity of other three antibodies was not affected. The costimulatory ability of G28-5 was shown to be differentially modulated when it was paired in combination with each of the four new anti-CD40 mAbs. MAbs 1.66 and especially 2.174 enhanced G28–5 costimulation, whereas 2.220 and 2.36 suppressed it.

Following selection based on evaluations in human in vitro systems, the four anti-CD40 mAbs were further examined for their suitability for in vivo evaluation in non-human primate studies. Two key points of analysis were the relative potency of each for binding to primate B cells and suppression of in vitro, T cell-dependent B cell antibody synthesis. It was found that all four mAbs crossreacted with cynomolgus macaque (*Macaca fascicularis*) B cells. 2.36 and 2.220 bound with higher avidity than 2.174 and 1.66. Lower apparent binding of mAbs 2.174 and 1.66 was not due to their particular isotypes, as other isotype-matched anti-CD40 mAbs demonstrated binding levels comparable to 2.36 and 2.220 (e.g., G28–5 and 2.118). These results were in contrast to that observed with human B cells where each of the mAbs demonstrated comparable binding. The ability of the four mAbs to suppress antibody synthesis by monkey B cells was found to parallel the ability to bind.

B. In Vivo Characterization

Two studies were performed in non-human primates using the murine anti-human CD40 mAbs to assess the suitability of anti-CD40 as an immunosuppressive agent and to select the appropriate antibody for further development. First, the in vivo clearance and acute toxicity of the four selected anti-CD40 mAbs were compared. These results were used to select two antibodies, 2.36 and 2.220, that were then tested in a second study designed to assess efficacy in the inhibition of the antibody response to a T-dependent antigen and acute toxicity.

Primate Efficacy Study with 2.36 and 2.220

Figure 2:
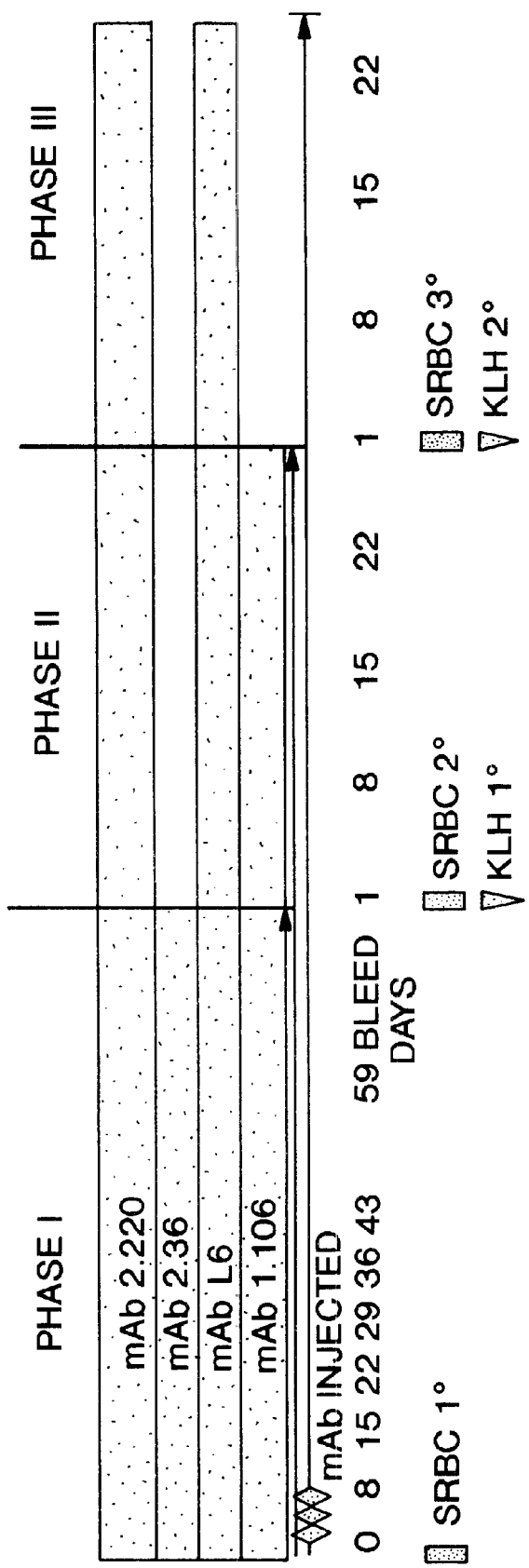
FIG. 2 is a schematic outlining the primate study protocol. Days of treatment are indicated with diamonds. Immunizations with SRBC and KLH are indicated with rectangles and triangles, respectively. Animals treated with 2.36 were not studied past Phase I and animals treated with 1.106 were not studied past Phase II.

Based upon previous findings, mAbs 2.36 and 2.220 were evaluated for their ability to suppress a T-dependent antibody response following intravenous administration to cynomolgus monkeys. This study was divided into three phases (FIG. 2). In Phase I, four groups consisting of one or two male and two female cynomolgus monkeys each were immunized intravenously on day I with sheep red blood cells (SRBCs), and then treated with 20 mg/kg of mAb 2.36, 2.220, 1.106 (IgG1 murine anti-human gp39, positive control), or L6 (IgG2a murine anti-human tumor antigen, negative control) on days 1, 3, and 5. IgM and IgG titers to the SRBC immunogen, serum levels of test and control articles, the presence of anti-test and control article antibodies, serum immunoglobulin levels, peripheral blood leukocyte counts, and the frequencies of various subpopulations of peripheral blood lymphocytes were determined. In phase II, after the control and test articles had cleared, the animals were immunized with SRBCs and a second antigen, keyhole limpet hemocyanin (KLH), to assess the induction of immunological tolerance and the reversibility of the observed immunosuppression. In phase III, selected animals were reimmunized to determine if the initially suppressed anti-SRBC antibody response recovered following an additional challenge with SRBCs and to assess the secondary antibody response to KLH.

An experiment was performed to show that MAb 2.220 significantly suppressed the primary antibody response to SRBCs (FIG. 3). Monkeys were treated with 20 mg/kg of either mAb 1.106, L6, 2.36 or 2.220 on Phase I Days 1, 3, and 5. Monkeys were immunized with SRBC on Day I of Phase I,II and III. FIG. 3a shows the results of serum samples that were analyzed for IgM anti-SRBC antibodies; FIG. 3b shows the results of serum samples that were analyzed for IgG anti-SRBC antibodies. Data are expressed as the geometric mean anti-SRBC titer for each group (n=3 or 4).

The peak primary response was inhibited 85% and 98% for IgM and IgG, respectively. Following clearance of mAb 2.220 in serum to below detectable levels, the peak secondary response to SRBCs was still inhibited 79% and 56% for IgM and IgG, respectively, compared to the negative control response in Phase I. This was in contrast to the positive control, mAb 1.106, with which a strong secondary antibody response to SRBCs was observed. The tertiary response to SRBCs was not inhibited, indicating that mAb 2.220 induced a prolonged immunosuppression, but not immunological tolerance. All animals immunized with KLH had a primary and secondary anti-KLH response, suggesting that the immunosuppression was reversible. Animals treated with 2.36 were not included in phase II because there was no significant inhibition seen in phase I of the study.

Mean peak serum concentrations, occurring immediately after the last dose, were 744 and 405 $\mu$g/ml for mAbs 2.220 and 2.36, respectively. Whereas mAb 2.36 cleared from the serum to below detectable levels by day 15, mAb 2.220 did not clear until day 29. Both mAbs 2.36 and 2.220 were immunogenic.

There were no drug-related clinical observations, changes in body weight or food consumption, or alterations in hematology or serum Ig levels in any animal. The only drug-related findings observed were transient 70% and 43% decreases in the percentages of peripheral B cells with mAbs 2.36 and 2.220, respectively. Recovery of B cells to normal levels occurred within 2–3 weeks post-treatment.

In summary, mAb 2.220 significantly suppressed the antibody response to SRBCs and 2.36 did not. Although mAb 2.220 induced a prolonged antigen-specific Immunosuppression, it was reversible. Based on these findings, mAb 2.220 was selected for further development.

EXAMPLE 2

Generation of Chimeric Antibody chi220

To address immunogenicity of the murine anti-human mAb 2.220, recombinant forms in which variable regions are fused to human constant regions were generated and compared for in vitro efficacy. The two approaches used were generation of a chimeric antibody, containing the unaltered murine variable regions, and humanized forms in which murine hypervariable regions (CDRs) are grafted on human framework sequences within the variable regions. Chimeric antibodies retain the antigen binding properties of parent antibody, but may have a greater likelihood of being immunogenic. Humanized antibodies are less likely to be immunogenic, but mutations introduced in the humanization can affect antigen binding.

A Construction and In Vitro Characterization of Chimeric and Humanized Antibodies The VL and VH regions from the anti-CD40 mAb 2.220 were obtained by PCR cDNA was generated from RNA isolated from the hybridoma expressing the 2.220 mAb using an IgG1-specific or a Ck-specific anti-sense primer to obtain the VH or VL regions, respectively. A poly-G tail was added to these single stranded cDNAs. The variable regions were then amplified by PCR using as a sense primer an oligonucleotide containing a poly-C sequence, complimentary to the poly-G tail, and a nested set of antisense primers. The PCR product obtained was then inserted into a bacterial vector using restriction sites included in the primers. Multiple clones were then sequenced by dideoxynucleotide sequencing. Two independent experiments were performed, beginning at the RNA stage and the sequences obtained were the same.

To generate a chimeric form of the antibody, the variable regions were amplified by PCR using primers that introduced a sequence encoding the signal sequence of the human antibody found to most closely match the 2.220 sequence, as shown in FIG. 4. The underlined portions of the light chain variable sequence (FIG. 4a) and the heavy chain variable sequence (FIG. 4b) designate the inserted signal sequences of the human antibody with the closest homology to murine 2.220. These PCR products were inserted into a vector containing sequences encoding the constant regions of human kappa or of human γ1 to generate complete light or heavy chain, respectively. The vectors also contained appropriate drug resistance genes for the generation and amplification of stable lines expressing the protein. Protein for initial characterization was produced by transient expression from COS cells followed by Protein A purification.

Figure 12A:
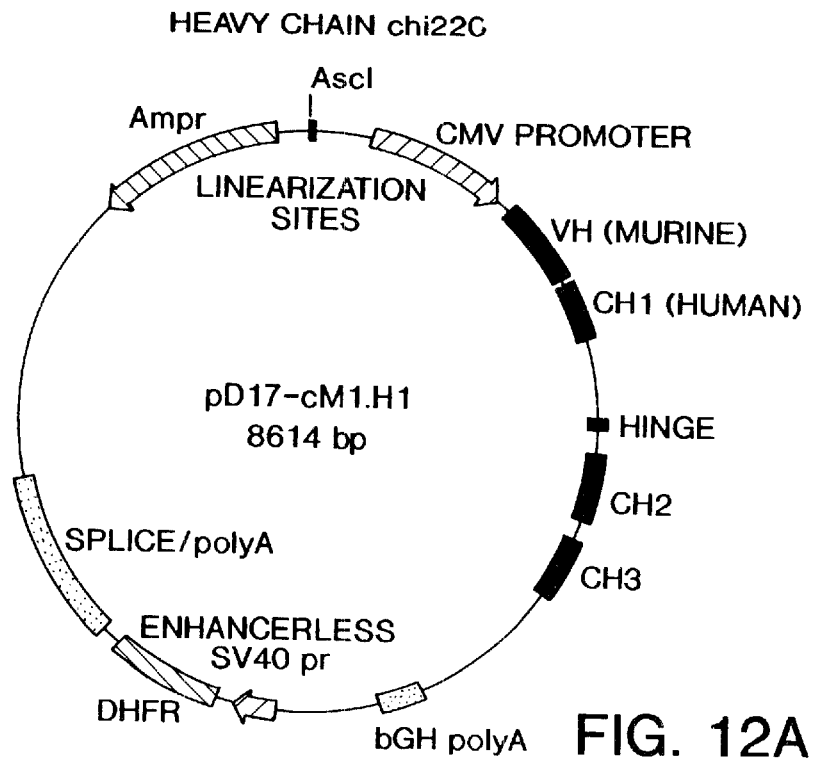
FIG. 12 shows expression vector maps for a heavy chain region and light chain region of a chimeric antibody of the present invention.
Figure 12B:
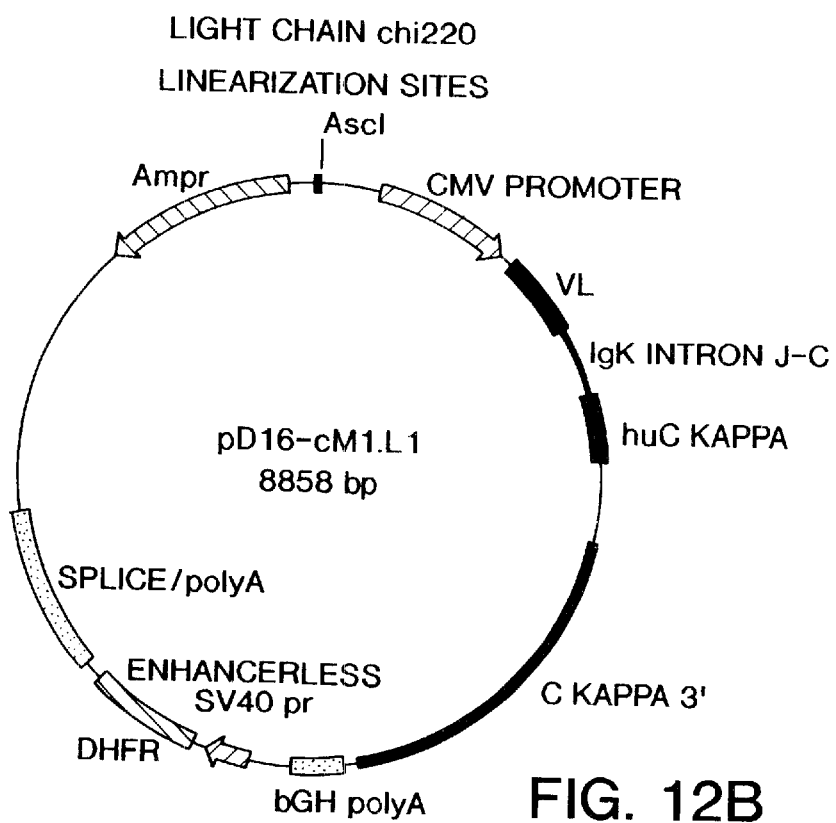

As an example, a chimeric antibody producing cell line was generated by co-transfecting CHO DG44 cells with separate expression vectors for the heavy and light chains of the chimeric antibody, and the high copy number electroporation method was used to promote co-integration. (See, U.S. Pat. No. 4,956,288). The chi220 heavy and light chains were cloned into the pD17 and pD 16 expression vectors, respectively. Both vectors are derived from the In Vitrogen™ plasmid pcDNA3, and contain the following features (FIG. 12): (1) the neomycin resistance gene from pcDNA3 was replaced with the murine dihydrofolate reductase (DHFR) gene under control of the enhancerless SV40 promoter (also referred to as the "weakened DHFR"; note that only the promoter was weakened, not the DHFR enzyme— the enhancerless promoter still contains the SV40 origin of replication, so these vectors can be used in transient COS transfections); (2) the gene of interest is expressed from the CMV promoter, and the poly adenylation signal is from the bovine growth hormone gene; (3) the expression cassette for the gene of interest is flanked by transcription termination sequences (i.e., 5' to the promoter and 3' to the poly A site); (4) the vectors contain two distinct restriction site polylinkers, one 3' to the promoter for cloning the gene of interest, and one 5' to the promoter for vector linearization prior to transfection; and (5) the ampicillin resistance gene and Co1E1origin for plasmid propagation in E. coli.

The heavy and light chain genes used were genomic constructs, with the following modifications: (1) the coding sequences for the heavy chain signal peptide, variable region and CH1 domain were contiguous (i.e., contained no introns); and (2) the coding sequences for the light chain signal peptide and variable region were contiguous.

Other expression vectors known by those skilled in the art, and capable of expressing a chimeric antibody of the present invention, are contemplated by the present invention. A nucleic acid sequence useful in an expression vector capable of expressing a heavy chain of a chimeric antibody of the present invention is shown in FIG. 13; a nucleic acid sequence useful in an expression vector capable of expressing a light chain of a chimeric antibody of the present invention is shown in FIG. 14.

The complete amino acid sequence of the heavy and light chains of the chimeric antibody ("chi220"), including the variable and constant regions, is as follows (the bold amino acids indicate variable heavy and variable light):

Heavy Chain Sequence (SEQ ID NO:3)

```
QIQLVQSGPE LKKPGETVRI SCKASGYAPT TTGMQWVQEM PGKGLKWIGW      50
INTHSGVPKY VEDFKGRPAP SLETSANTAY LQISNLKNED TATYFCVRSG     100
NGNYDLAYFA YWGQGTLVTV SAASTKGPSV FPLAPSSKST SGGTAALGCL     150
VKDYFPEPVT VSWNSGALTS GVHTFPAVLQ SSGLYSLSSV VTVPSSSLGT     200
QTYICNVVHK PSNTKVDKKV EPKSCDKTHT CPPCPAPELL GGPSVFLFPP     250
KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE     350
PQVYTLPPSR DELTKNQVSL TCLVKGFYPS DIAVEWESNG QPENNYKTTP     400
PVLDSDGSFF LYSKLTVDKS RWQQGNVFSC SVMHEALHNH YTQKSLSLSP     450
GK                                                         452
```

Light Chain Sequence (SEQ ID NO:4)

```
DIVLTQSPAT LSVTPGDRVS LSCRASQSIS DYLHWYQQKS KESPRLLIKY      50
ASHSISGIPS RFSGSGSGSD FTLSINSVEP EDVGIYYCQH GKSFPWTPGG     100
GTKLEIKRTV AAPSVFIFPP SDEQLKSGTA SVVCLLNNFY PREAKVQWKV     150
DNALQSGNSQ ESVTEQDSKD STYSLSSTLT LSKADYEKHK VYACEVTHQG     200
LSSPVTKSFN RGEC                                            214
```

Figure 5A:
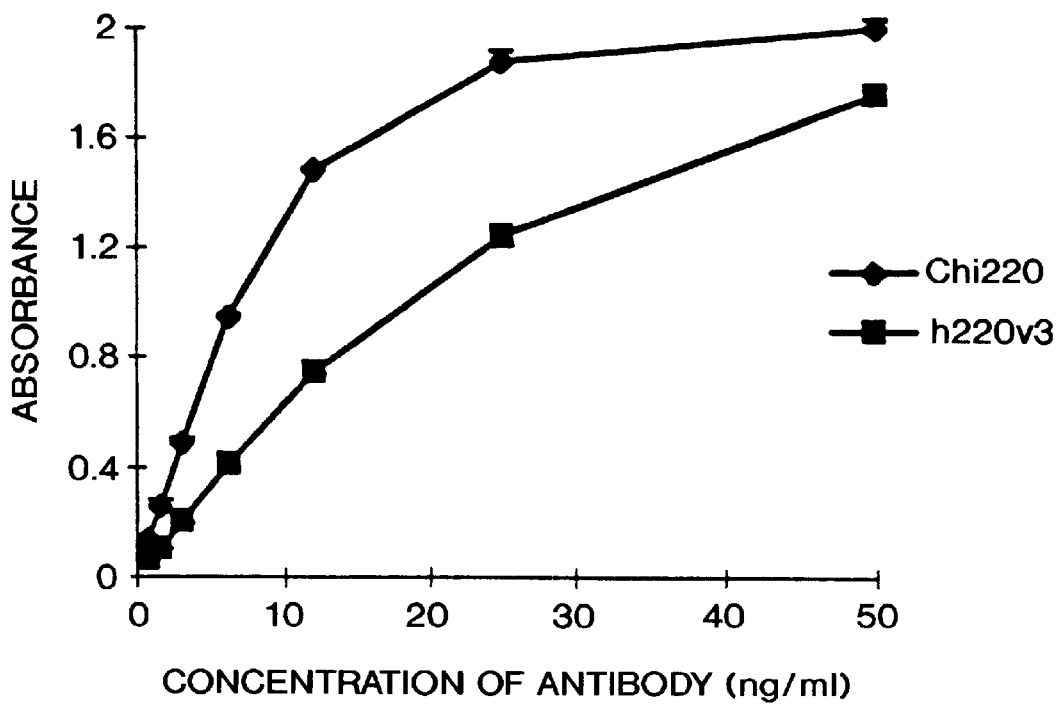
FIG. 5a shows the binding of chi220 and h220v3 to hCD40-mG2b in an ELISA based assay.

Several humanized forms of 220 were generated. This process involves the identification of murine and human germline sequences with the closest homology to the VH and VL domains. The murine germline sequences were used to identify likely locations of somatic mutations that have arisen during the process of affinity maturation. The human sequences were then used as template and regions of the sequence known or suspected to be important to the binding specificity are replaced in the human sequences for both VH and VL. The structures of these sequences were then modeled using as a template the protein with the closest homology for which a crystal structure has been solved. Plasmids encoding the humanized forms were generated using PCR directed mutagenesis and used to generate antibody by transient expression from COS cells. In vitro assays were performed with the chimeric and humanized antibodies of the present invention, and results are depicted in FIG. 5. FIG. 5a shows the results of a binding assay testing the binding of chi220 and h220v3 to hCD40-mG2b in an ELISA based assay. Wells of Immunlon® II microtiter plates (Dynex) were coated with hCD40-mG2b at a concentration of 10 ng/ml in PBS for 2 hrs. Wells were blocked with Specimen Diluent (Genetic Systems), and antibodies were added at the indicated concentrations. Following a 1hr incubation, wells were washed, and the presence of the antibody detected using peroxidase-conjugated goat anti-human IgG antibody. H220v3 is a humanized form of mAb 2.220. Values are the average of duplicate wells and error bars represent the standard deviation.

Figure 5B:
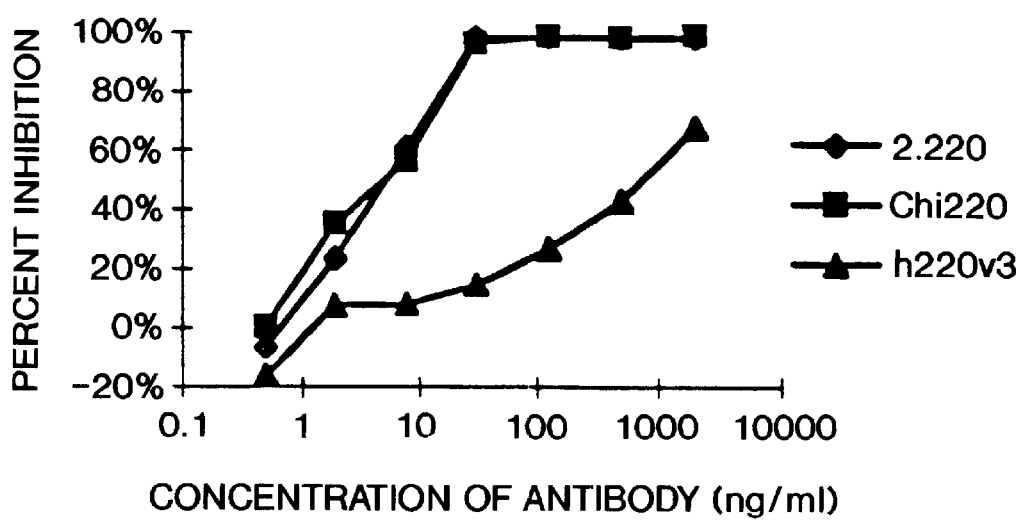
FIG. 5b shows the inhibition of sgp39-mediated costimulation of human B cells with anti-human CD40 mAbs.

FIG. 5b shows the results of an assay testing the inhibition of sgp39-mediated costimulation of human B cells with anti-human CD40 mAbs. Resting human tonsillar B cells (50,000/well) were incubated with sgp39 fusion protein, 20 μg/ml rabbit anti-human IgM coated immunobeads and the indicated concentrations of the anti-CD40 mAbs or medium only control in 96 well plates. 72 hrs after initiation of cultures, all wells were pulsed with 1 uCi/well [$^3$H] thymidine and the cells cultured for an additional 18 hrs. Cells were then harvested and incorporated [$^3$] thymidine measured in a scintillation counter.

Based upon the results of in vitro assays (FIGS. 5a and 5b, that show both the chimeric and humanized antibody effectively bound CD40 and inhibited B cell stimulation) the chimeric antibody was chosen for further study.

EXAMPLE 3

Efficacy of chi220

A. Chimeric mAb 2.220: Single-Dose Efficacy Study in Nonhuman Primates Chi220 was evaluated in cynomolgus monkeys for its ability to suppress primary and secondary humoral immune responses to T cell-dependent antigens. In one study, groups of four monkeys were immunized with sheep erythrocytes (SRBCs) and given a secondary immunization of ovalbumin (OVA) immediately prior to receiving a single intravenous bolus dose of either chi220 at 10, 40, or 100 mg/kg or sterile phosphate buffered saline (PBS) as a control. Substantial suppression of the primary humoral immune response against SRBCs was observed at all three dose levels, demonstrating efficacy of chi220 in primates. A dose-dependent transient depletion of peripheral blood B cells was observed in all of the chi220-treated monkeys, with the time to recovery also being dose dependent. At the two highest doses, transient mild decreases in the group mean absolute numbers of peripheral blood T cells were observed. Transient minimal decreases in serum IgM levels were observed, with no drug related changes in serum levels of IgG or IgA.

To assess the induction of immunological tolerance and reversibility of immunosuppressive activity, all monkeys were immunized with OVA, SRBCs, and a neoantigen, keyhole limpet hemocyanin (KLH) on day 149, when serum levels of chi220 in the 100 mg/kg group were below levels believed to be immunosuppressive (~10 µg/ml) and the numbers of peripheral blood B cells had returned to predose levels. The anti-SRBC response at the lowest dose level was generally comparable to the primary anti-SRBC antibody response in the control monkeys. However, the antibody response to SRBCs was still partially or substantially suppressed in the monkeys treated at the two higher dose levels.

To further explore the dose dependence of immunosuppression and B cell depletion, a second study was performed in which additional monkeys (four/group) were immunized with SRBCs, and then given a single dose of chi220 at 0.1 or 1.0 mg/kg or PBS. Suboptimal immunosuppression of the antibody response to SRBCs was observed at both dose levels. Moderate depletion of peripheral blood B cells was evident in monkeys that received 1.0 mg/kg chi220 by Day 8, reversing by Day 29. At 0.1 mg/kg, a decrease in the mean number and percentage of peripheral blood B cells was observed, but values were not outside the normal historical ranges for percent B cells. Historical limits have not been established for absolute numbers of peripheral blood B cells. Transient minimal decreases in peripheral blood T cell numbers and mild decreases in ex vivo T cell proliferation were observed in monkeys that received 1 mg/kg chi220. Finally, there was no evidence of complement activation or drug-related changes in the serum levels of IL-6 or TNFα. Ex vivo T cell activation, complement activation, and serum cytokine levels were not assessed in monkeys treated with 10, 40, or 100 mg/kg chi220.

In both studies, serum samples were examined following chi220 administration for circulating levels of test article, and to assess antibody formation against the test article. Pharmacokinetic analysis indicated that the mean peak serum concentration (Cmax) of chi220 did not increase in a manner proportional to the dose increment, and that the half-life of chi220 became prolonged as the dose administered was increased. Chi220 was found to be immunogenic when administered at 0.1, 1 or 10 mg/kg. At circulating concentrations above 10 mg/ml, it appears that chi220 can suppress the antibody response directed against it.

1. Experimental Protocol

In the initial study mentioned above, cynomolgus monkeys were assigned to four groups consisting of two males and two females each. All monkeys were immunized 28-days prior to chi220 or control article administration with OVA (5 mg/kg, im and 10 mg/kg, sc). On Day 1, all monkeys were immunized with SRBCs (1.7 ml/kg of a 10% suspension, iv) and given a secondary immunization of OVA (5 mg/kg, im and 10 mg/kg, sc) immediately prior to receiving a single intravenous bolus dose of either chi220 at 10, 40, or 100 mg/kg or sterile PBS as a control. On Day 149, after the serum levels of chi220 had fallen below putatively immunosuppressive levels (~10 µg/ml) and the levels of peripheral blood B cells had returned to predose levels in all groups, the monkeys were immunized with OVA, SRBCs, and KLH (10 mg/animal, im). The purpose of the KLH immunization was to show that the monkeys were able to mount an immune response to a neoantigen after being treated with chi220.

In order to demonstrate a better dose response with respect to immunosuppression and peripheral blood B cell depletion, additional monkeys in a second study (two/sex/ group) were immunized with SRBCs, and then given a single dose of either chi220 at 0.1 or 1.0 mg/kg or PBS as a control on Day 1. Hematological parameters and peripheral blood lymphocyte subpopulations were monitored at selected time points during both studies. Serum chemistry parameters were monitored in monkeys that received 10, 40, or 100 mg/kg chi220, but were not monitored at the 0.1 and 1 mg/kg dose levels because no drug-related findings were observed at the higher doses. In addition, serum levels of IgM, IgG, IgA, and chi220 were measured. To assess efficacy, specific IgM and IgG antibody formation against the SRBC and OVA immunogens was determined on the appropriate serum samples obtained just prior to immunogen administration and weekly thereafter. Specific IgM and IgG antibody formation against the test article for monkeys that received chi220 was determined prior to test article administration on Day 1, and weekly thereafter. Geometric mean titers were used when comparing antibody responses between groups. In addition, total hemolytic complement activity ($CH_{50}$) and C4d fragment levels were measured, and TNFα and IL-6 levels were determined in monkeys that received 0.1 or 1 mg/kg chi220 at selected time points following chi220 administration. Ex vivo peripheral blood T cell activation was also assessed following stimulation with concanavalin A in monkeys receiving 0.1 and 1 mg/kg chi220 on Days 17 and 31 to assess the effects of chi220 on T cell responsiveness to a mitogen. Finally, all monkeys were observed daily for clinical signs of toxicity, body weights recorded weekly, and food consumption monitored daily.

Monkeys were immunized with SRBC prior to receiving vehicle or 10, 40, or 100 mg/kg chi220 (FIG. 6a) or 0.1 or 1 mg/kg chi220 (FIG. 6b) on Day 1. Serum samples were analyzed for IgM anti-SRBC antibodies by ELISA. Data are expressed as the geometric mean anti-SRBC antibody endpoint titer (EPT) for each group (n=2 [100 mg/kg group beyond Day 15] or 4), where EPT is equivalent to the reciprocal of the greatest dilution of serum with an absorbance of greater than two times the mean plate background.

2. Results a Anti-SRBC Antibody Response

Figure 7A:
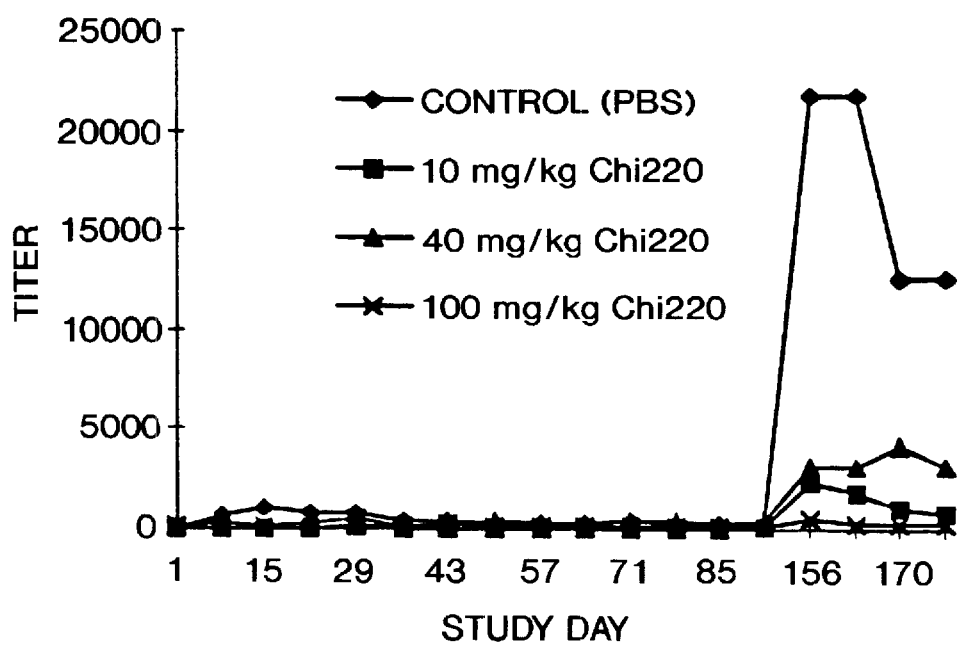
FIG. 7a shows the results from monkeys that received 10, 40 or 100 mg/kg chi220.

When administered to monkeys at 10, 40, or 100 mg/kg, chi220 was effective at substantially suppressing the primary antibody response against SRBCs. On the peak day of the control primary IgM anti-SRBC antibody response (Day 8), the mean primary IgM anti-SRBC antibody response was suppressed approximately 92–94% in the monkeys treated with 10, 40, and 100 mg/kg chi220, compared to controls (FIG. 6a). The group mean IgM anti-SRBC antibody response did not become positive through Day 85 at the 10, 40 or 100 mg/kg dose levels. On the peak day of the control primary IgG anti-SRBC antibody response (Day 15), the mean primary IgG anti-SRBC antibody response was suppressed 98%, 99%, and 85% in monkeys that received 10, 40, and 100 mg/kg, respectively, compared to controls (FIG. 7a). Higher overall predose anti-SRBC antibody titers in the 100 mg/kg group may have accounted for the apparent lack of dose-dependent immunosuppression. Overall, monkeys treated with 10 or 100 mg/kg chi220 did not mount a primary IgG anti-SRBC antibody response through Day 85. However, two of the monkeys treated with 40 mg/kg chi220 had a delayed primary IgG antibody response to SRBCs (comparable to the control response in magnitude), which became positive by Day 36 and peaked on Day 51.

On Day 149, after the serum levels of chi220 had fallen below putatively immunosuppressive levels (~10 µg/ml) and the levels of peripheral blood B cells had returned to predose levels in all groups, the monkeys were immunized a second time with SRBCs. As expected, control monkeys mounted a strong secondary IgG antibody response to SRBCs. Monkeys treated with 10 mg/kg chi220 mounted primary IgM and IgG antibody responses to SRBCs that were generally comparable to the primary antibody response in the control monkeys. However, the antibody response to SRBCs was still partially suppressed at the 40 mg/kg dose level and substantially suppressed at the 100 mg/kg dose level. Although two monkeys treated with 40 mg/kg chi220 that had previously mounted weak primary antibody responses to SRBCs developed IgM and IgG anti-SRBC antibody titers characteristic of a secondary antibody response, the anti-SRBC antibody responses in the two other monkeys in that group and the remaining monkeys treated with 100 mg/kg chi220 was still approximately 90% suppressed compared to the mean primary anti-SRBC antibody response of the control monkeys.

Figure 7B:
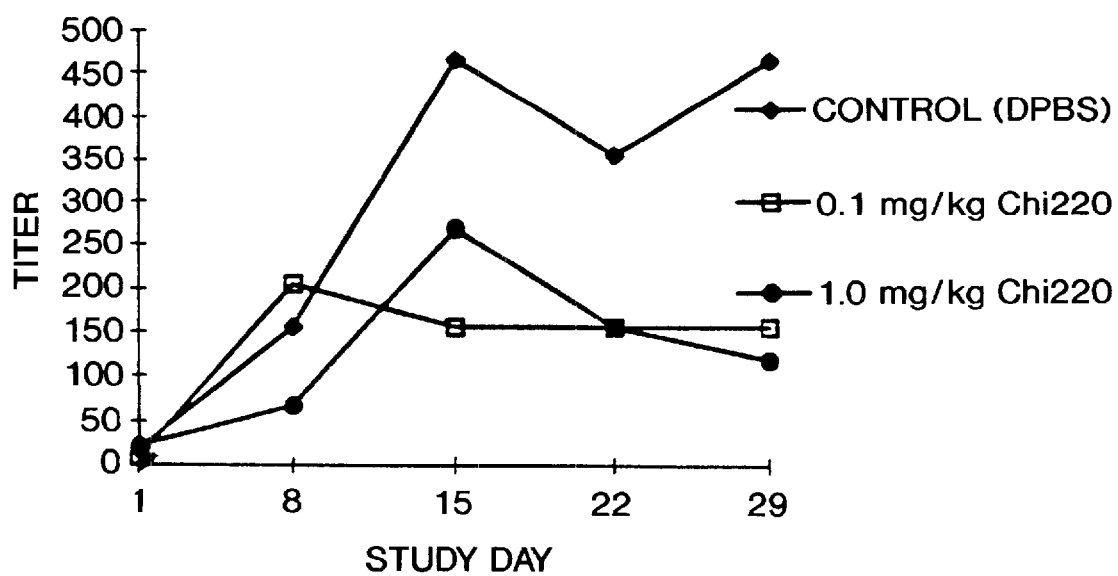
FIG. 7b shows the results from monkeys that received 0.1 or 1 mg/kg chi220.

Suboptimal immunosuppression of the antibody response to SRBCs was observed following administration of 0.1 or 1.0 mg/kg chi220 (FIGS. 6b and 7b). While all of the chi220-treated monkeys mounted a positive IgM antibody response to the SRBC antigen, the overall mean peak IgM anti-SRBC antibody response was suppressed approximately 56% in the monkeys treated with 1 mg/kg chi220 compared to the mean peak control response. No suppression of the IgM anti-SRBC antibody response was observed in monkeys treated with 0.1 mg/kg chi220. The mean IgM anti-SRBC antibody response peaked on Day 15 in the control monkeys, and on Day 8 in the monkeys that received 0.1 and 1.0 mg/kg chi220. Overall, the mean peak IgG anti-SRBC antibody response was suppressed 56% and 42% in the monkeys treated with 0.1 and 1.0 mg/kg chi220, respectively. The mean IgG anti-SRBC antibody response peaked on Day 15 in the control monkeys and monkeys treated with 1 mg/kg chi220, and on Day 8 in the monkeys that received 0.1 mg/kg chi220.

b. Anti-OVA Antibody Response

Figure 8A:
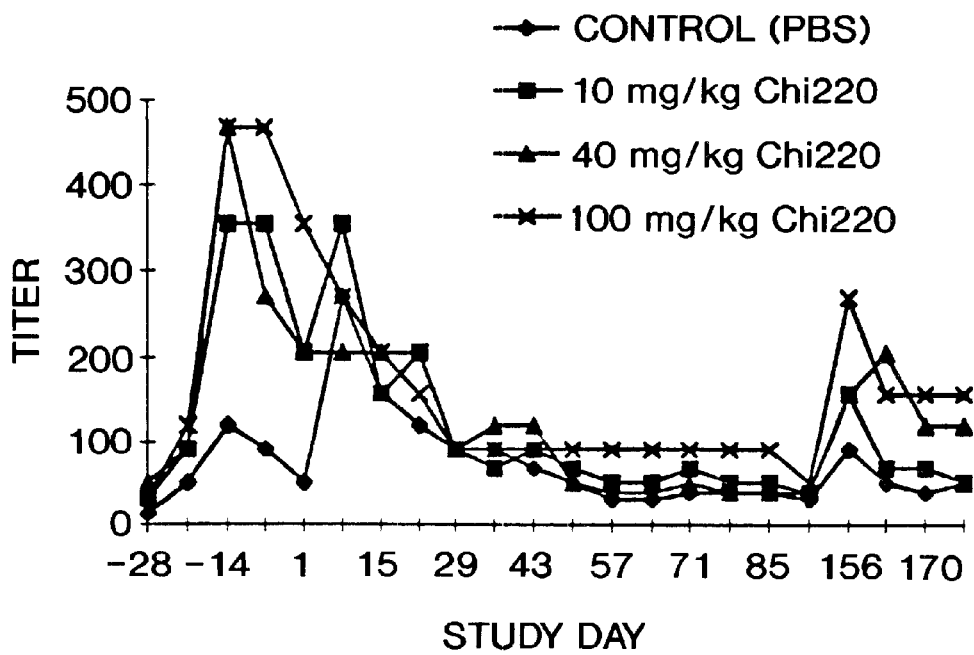
FIG. 8a shows the results of analysis for IgM anti-OVA antibodies.
Figure 8B:
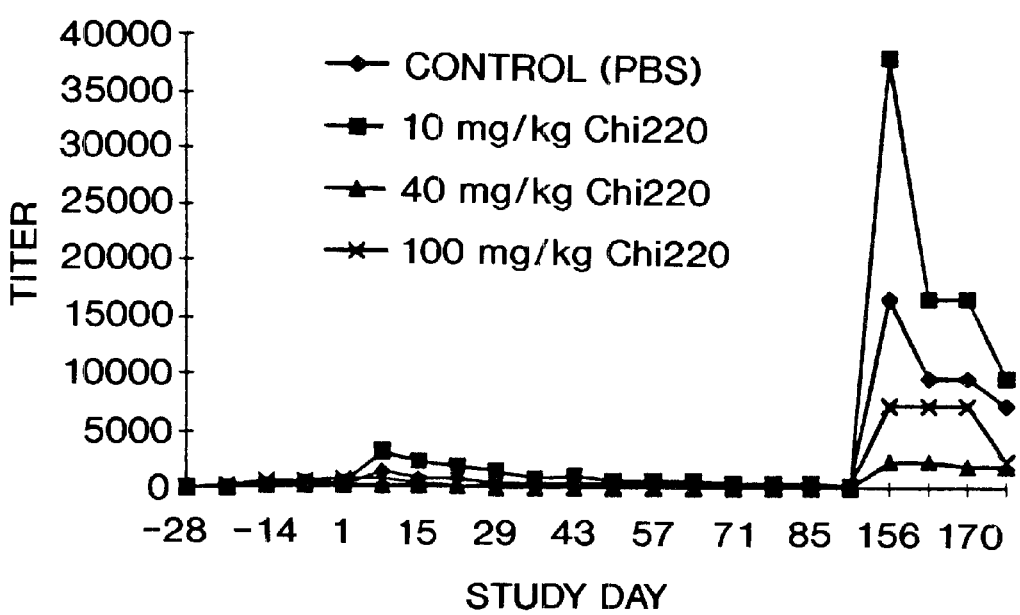
FIG. 8b shows the results of analysis for IgG anti-OVA antibodies.

Monkeys were administered an intravenous dose of 10, 40, or 100 mg/kg chi220 on Day 1. In addition all monkeys were immunized with OVA on Days -28, 1, and 149. Serum samples were analyzed for IgM (FIG. 8a) or IgG (FIG. 8b) anti-OVA antibodies. Data are expressed as the geometric mean anti-OVA endpoint titer (EPT) for each group (n=2 [100 mg/kg group beyond Day 15] or 4), where EPTs are equivalent to the reciprocal of the greatest dilution of serum with an absorbance of greater than two times the mean plate background.

Specific IgM and IgG antibody formation against OVA was monitored weekly during the study in monkeys that received 10, 40, or 100 mg/kg chi220. The primary and secondary anti-OVA antibody responses were highly variable and generally weak in all monkeys (FIG. 8). Monkeys scheduled to receive chi220 on Day 1 had greater anti-OVA antibody titers than monkeys in the control group.

On Day 149, the monkeys were given a tertiary OVA immunization. All of the monkeys mounted positive IgG antibody responses to OVA within 7 days following challenge. Control monkeys and monkeys treated with 10 mg/kg chi220 had antibody titers characteristic of a tertiary antibody response, whereas monkeys treated with either 40 or 100 mg/kg chi220 developed antibody titers that were more characteristic of a secondary antibody response.

C. Anti-KLH Antibody Response

Figure 9A:
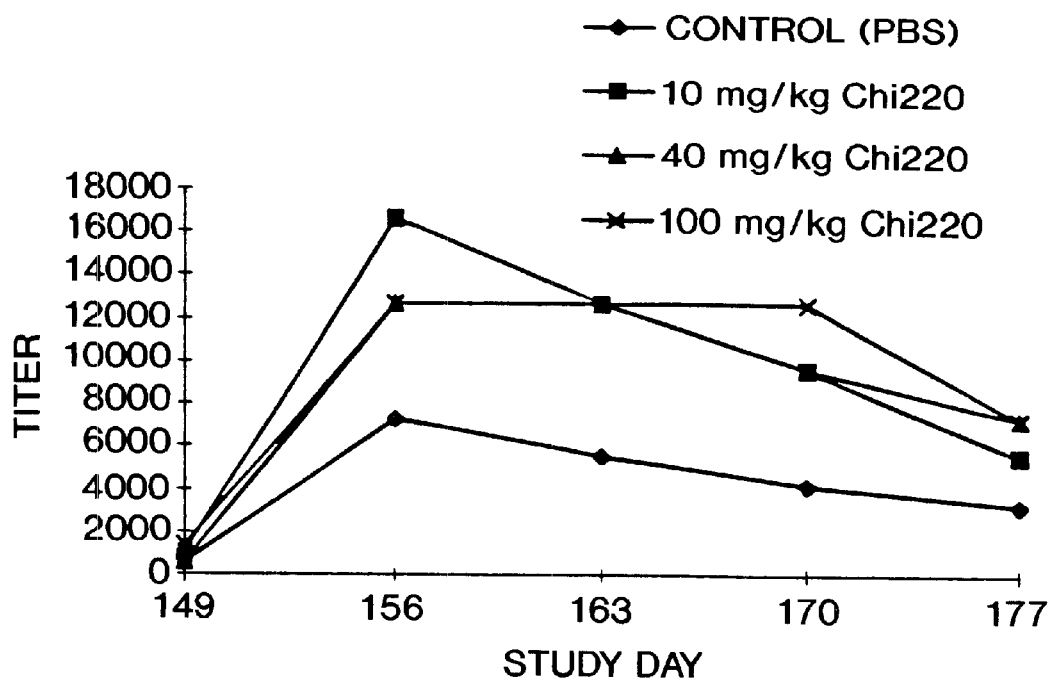
FIG. 9a shows the results of analysis for IgM anti-KLH antibodies.
Figure 9B:
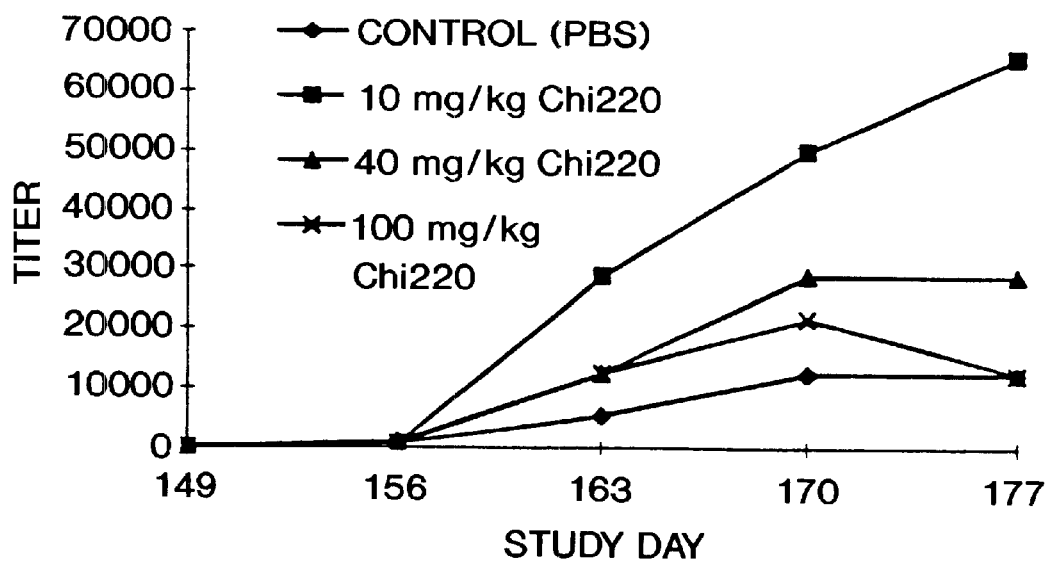
FIG. 9b shows the results of analysis for IgG anti-KLH antibodies.

Monkeys were administered an intravenous dose of 10, 40, or 100 mg/kg chi220 on Day 1. In addition, all monkeys were immunized with KLH on Day 149. Serum samples were analyzed for IgM (FIG. 9a) or IgG (FIG. 9b) anti-KLH antibodies. Data are expressed as the geometric mean anti-KU endpoint titer (EPT) for each group (n=2[100 mg/kg group beyond Day 15] or 4), where EPTs are equivalent to the reciprocal of the greatest dilution of serum with an absorbance of greater than two times the mean plate background.

On Day 149, after the serum levels of chi220 had fallen below putatively immunosuppressive levels (~10 µg/ml) and the levels of peripheral blood B cells had returned to predose levels in all groups, the monkeys were immunized with KLH (10 mg/animal, im). All monkeys mounted positive IgM and IgG antibody responses to KU, demonstrating that the ability to respond to a new antigen was not compromised (FIG. 9).

d. Serum Levels of Test Article and Anti-Test Article Antibody Response

Serum samples were examined following chi220 administration to determine circulating levels of test article and to assess antibody formation against the test article. The mean peak serum concentration (Cmax) of chi220 occurred three minutes following the administration of 10 or 40 mg/kg doses and six hours following administration of the 100 mg/kg dose. Cmax values of chi220 were 329, 2429, and 2343 µg/ml in the monkeys treated with 10, 40, or 100 mg/kg chi220, respectively. There was, however, considerable variation in the Cmax of individual monkeys in the 40 and 100 mg/kg groups. The mean serum half-life of chi220 was estimated to be approximately 114, 173 and 315 hours in monkeys treated with 10, 40, or 100 mg/kg chi220, respectively.

Mean Cmax values, occurring three minutes following chi220 administration, were 1.77 and 33 µg/ml for 0.1 and 1 mg/kg doses, respectively. No gender related differences in the serum levels of chi220 were observed within each dose level. Mean $AUC_{inf}$ values were 15.5 and 847 µg/ml, for 0.1 and 1 mg/kg doses, respectively. Taken together, the studies suggest that the half-life of chi220 becomes prolonged as the dose administered is increased. Furthermore, it appears that the Cmax of chi220 increases in a manner disproportionate to the dose increment.

Although the IgM anti-test article response was minimal or absent in the monkeys that received 10, 40, or 100 mg/kg chi220, a significant IgG anti-test article antibody response was observed in the monkeys that received 10 mg/kg chi220. The mean IgG anti-test article antibody response in the monkeys that received 10 mg/kg chi220 became positive on Day 29, approximately I week after the mean group serum concentration of chi220 had fallen below 10 µg/ml, and peaked on Days 36 and 43 at a geometric mean titer of 12,627. The appearance of IgG anti-test article antibodies in the monkeys that were treated with 10 mg/kg chi220 also coincided with the first detectable increases in B cell numbers following depletion. By the last day measured (Day 149), the monkeys that received 40 or 100 mg/kg chi220 had still not mounted a positive antibody response against chi220, although the group mean chi220 serum levels were below 10 µg/ml by Day 57 (40 mg/kg group) or Day 92 (100 mg/kg group).

Chi220 was immunogenic when administered at 0.1 or 1 mg/kg. Three of four monkeys that received either 0.1 or 1 mg/kg chi220 had weakly positive IgM anti-test article antibody responses by Day 15 during the study. Three of four monkeys treated with 1 mg/kg chi220 had significant IgG anti-test article antibody responses by Day 22, peaking at a geometric mean endpoint titer of 16,618. Overall, the geometric mean IgG anti-test article antibody response was not positive in the monkeys that received 0.1 mg/kg chi220, and only one monkey that received 0.1 mg/kg chi220 had a weakly positive IgG anti-test article antibody response, peaking at an endpoint titer of 2430 on Day 22. Collectively, these data suggest that chi220 is capable of immunosuppressing an antibody response against itself at serum levels of greater than approximately 10 $\mu$g/ml.

EXAMPLE 4

Mouse Model System

Applicants also developed and tested in vivo a rat anti-murine CD40 mAb designated 7E1-G2b and its predecessor, 7E1-G1. The generation of this antibody was performed in order to explore the potential of anti-CD40 therapy in murine models of auto immune, inflammatory and transplant disease. The primary objective of the mouse model system was to generate an anti-murine counterpart that mimicked 2.220's complete and potent blockade of gp39/CD40 interaction while possessing weak costimulatory activity, and test it in vivo in standard experimental disease models.

A Isolation and Characterization of Anti-Murine CD40 Monoclonal Antibodies 7E1-G1 and 7E1-G2b 1. Immunization, Fusion and Characterization A recombinant murine CD40 immunoglobulin fusion protein consisting of the extracellular region of mouse CD40 fused to the hinge, CH2 and CH3 domains of a mouse IgG2a antibody (mCD40-mIg) was used to immunize an 8 week old female Lewis rat via footpad inoculation. Three days following the last immunization, leukocytes from the draining lymph nodes were fused with X63-Ag8.653 mouse myeloma cells to create rat x mouse heterohybridomas. Wells containing antibody specific for native mouse CD40 were identified for reactivity with the original mCD40-mIg immunogen by ELISA, and for reactivity with a CD40 positive mouse B cell lymphoma cell line (WEHI-231, ATCC CRL-1702). Supernatants were then tested for the ability to inhibit the binding of mCD40-mIg to soluble, recombinant mCD8-murine gp39 fusion protein, mgp39, the murine equivalent of sgp39. Approximately twelve of the most potent inhibitor master wells were cloned by a limiting dilution method.

Following cloning, functional assays were performed with culture supernatants and purified antibody in order to more accurately assess the ability of the anti-CD40 mAbs to inhibit the interaction of murine gp39 with CD40 and to determine their stimulatory properties. Inhibitory properties were measured by the ability to inhibit the binding of mgp39 to WEHI-231 using standard procedures known in the art. Stimulatory properties were measured by the induction of tight, homotypic adhesion of WEHI-231 cells and the proliferation of splenic B cells in the presence of the antibody and anti-IgM using procedures known in the art. From these results, three mAbs (5A3, 7E1-G1 and 8E1) were determined to be most like the anti-human CD40 mAb2.220 with respect to gp39/CD40 blockade and level of costimulatory activity.

2. Selection of 7E1 as the Lead Anti-Murine CD40 mAb

In vivo studies in mice were aimed at identifying which of the blocking/non-stimulatory anti-CD40 mAbs most potently suppressed specific antibody responses to a T-dependent antigen. Suppression of the IgG antibody response to SRBCs in mice with anti-murine CD40 mAb was studied. Groups of five BALB/c mice were immunized IV with 1×10$^8$ SRBCs and concurrently treated ip with 1 mg of anti-murine CD40 mAbs 5A3, 7E1-G1 or 8E1. As controls, groups of similarly immunized mice were treated with MR1 (hamster anti-murine gp39, positive control, 250 ug), 6E9 (rat anti-human gp39, negative control, 1 mg) or PBS. Mice were evaluated for IgG anti-SRBC titers by ELISA on days 7, 14, 21 and 35. The results indicated that when administered as a single dose of antibody at the time of antigen challenge with SRBCs, mAb 7E1-G1 was shown to be a more effective suppressor of the IgG anti-SRBC response compared to mAbs 5A3 or 8E1, and was therefore selected as the lead anti-CD40 mAb for murine studies.

3. Isotype Switch Variant of mAb 7E1-G1

7E1-G1 did not possess effect or function characteristics comparable to that of the chimeric 2.220 anti-human CD40 mAb (i.e., rat IgG1 is not as efficient as human IgG1 at complement fixation and Fc receptor interaction) and the profile of specific antibody suppression in vivo for 7E1 was not as complete as that seen with the 2.220 mAb in primates. Thus, an antibody having 7E1 specificity but with a rat isotype more like human IgG1 in its effect or capabilities was sought. To this end, a natural isotype switch variant of 7E1, from an IgG1 to an IgG2b, was generated by the sib-selection technique (Hale et al., *J. Immunol.* Methods (1987) 103(1):59–67). Briefly, an anti-CD40 mAb of the IgG2b isotype was identified by ELISA among supernatants of 96 well plates that had been seeded at 1000 cells/well with the original 7E1 hybridoma. Subsequent rounds of plating and identification of IgG2b positive wells at seeding densities of 200 and then 20 cells/well followed by two rounds of cloning by limiting dilution led to the isolation of a clonal IgG2b switch variant of 7E1, 7E1-G2b. 7E1-G2b is a legitimate switch variant of the IgG1 as demonstrated by three sets of data First, N-terminal sequencing of the heavy chain showed that both versions were identical for the first 35 amino acid residues. Second, PCR analysis using primers specific for the variable heavy chain CDRs of 7E1-G1 yielded a band of appropriate size from cDNA obtained from either 7E1-G1 or 7E1-G2b, and not two other unrelated antibodies. Lastly, assessment of binding activity of purified lots of the two versions to immobilized mCD40-hIg in an ELISA using an anti-kappa tracer reagent yielded essentially identical titration curves.

B. In Vivo Studies

1. In Vivo Comparison of 7E1-G1 to 7E1-G2b in Antibody Response Model

Figure 10A:
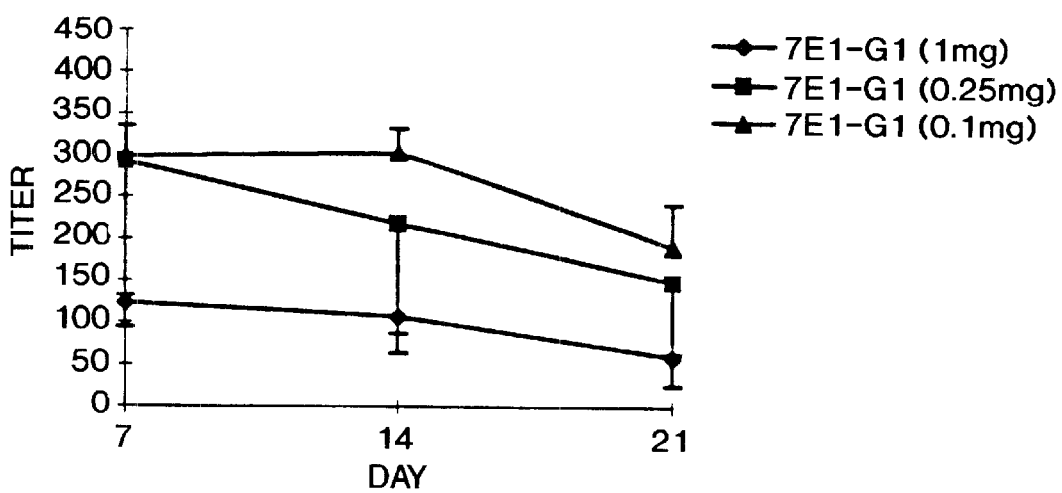
FIG. 10 shows a comparison of the ability of antibody 7E1-G1 and 7E1-G2b to suppress an IgG antibody response to SRBC.
Figure 10B:
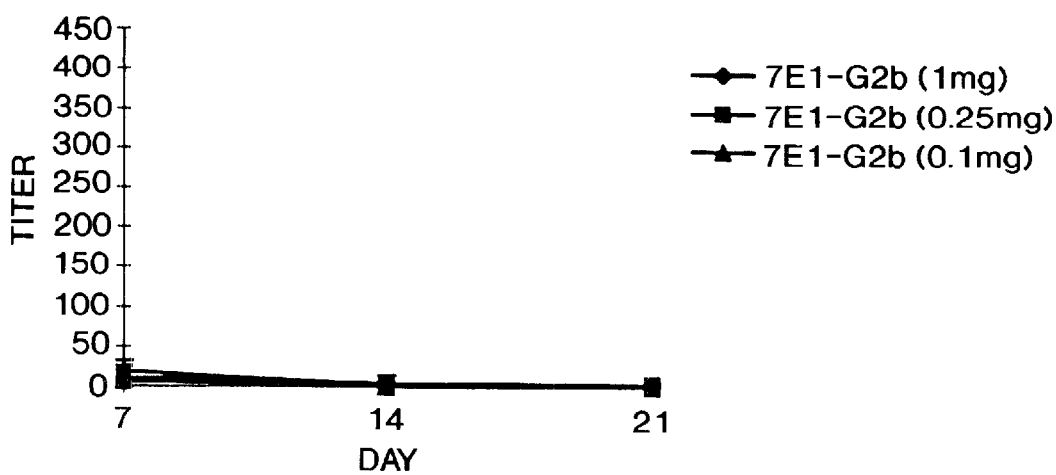
Figure 10C:
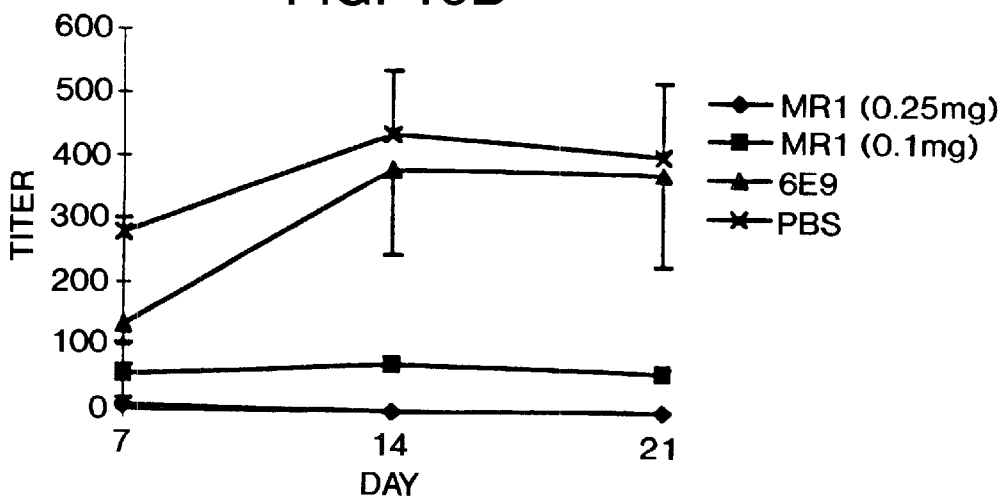

7E1-G1 was compared to 7E1-G2b for efficacy in vivo using SRBC's as the T cell dependent antigen. Groups of three to five animals were immunized iv with SRBC and concurrently treated ip with the antibody 7E1-G1 or 7E1-G2b, at 1, 0.25, or 0.1 mg of compound on day 0 as indicated in FIG. 10. Anti-murine gp39 mAb MR1 served as a positive control for immunosuppressive effect. MAb 6E9 and PBS served as irrelevant mAb and no mAb controls, respectively. Mice were evaluated for anti-SRBC titers by ELISA on days 7, 14 and 21. Titer represents the calculated dilution of serum to yield an OD value=0.3 in the ELISA. As shown in FIG. 10, 7E1-G2b suppressed the IgG response to SRBCs at doses where the 7E1-G1 did not.

2. 7E1-G2b Dose Response in T-dependent Antigen Mouse Model

7E1-G2b was examined in a T cell dependent primary immune response model using SRBC as the antigen. 7E1-

Figure 11:
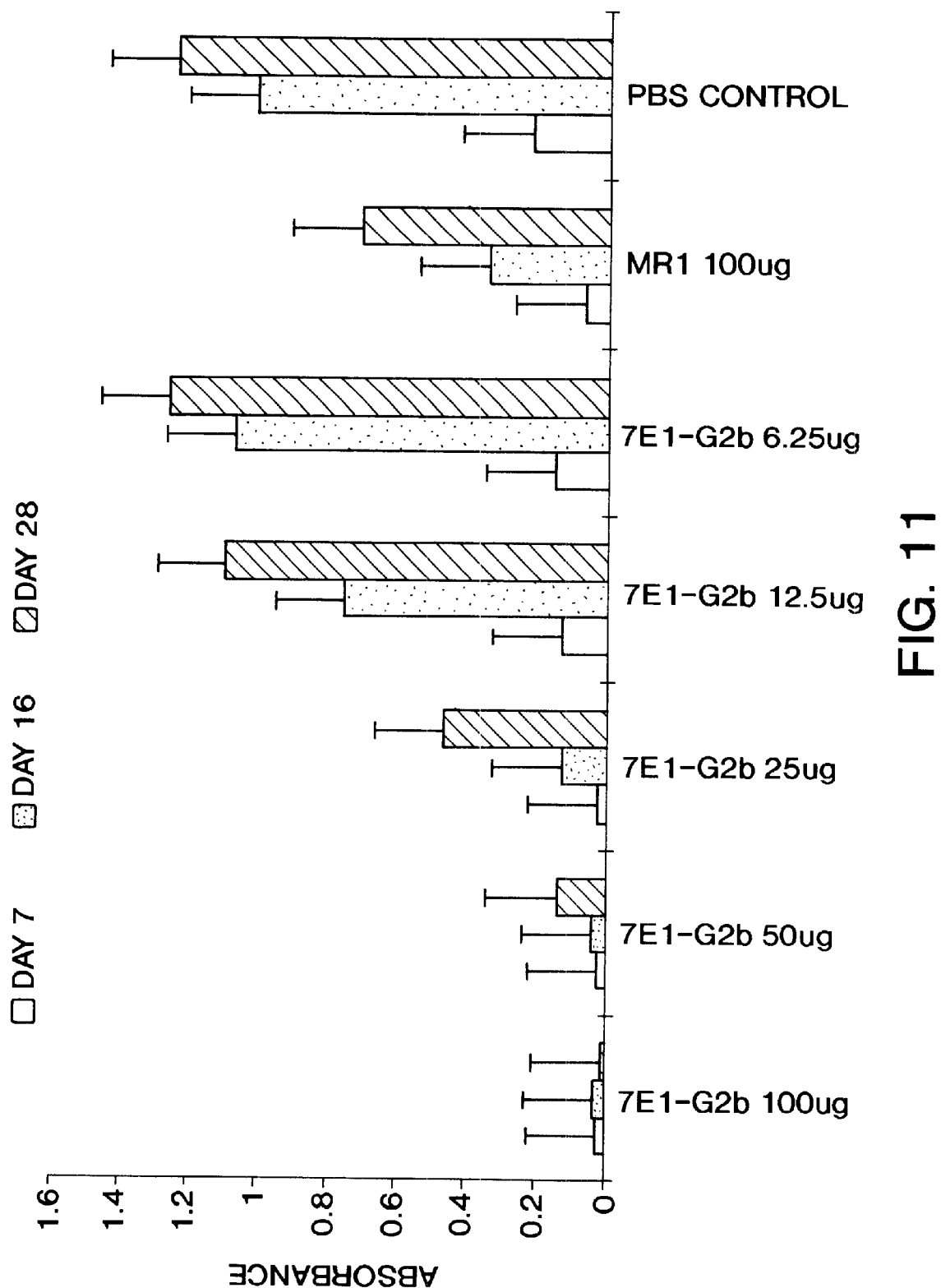
FIG. 11 shows the dose response of inhibition of antibody response to SRBC with 7E1-G12b.

G2b was tested at various doses to determine the lowest effective dose. BALB/c mice (n=5) were injected IV with $1\times10^8$ SRBCs and treated with a single injection of 7E1-G2b at the indicated doses or MR1 (anti-murine gp39) or PBS administered at the same time as the antigen on day 0. Shown in FIG. 11 is the IgG anti-SRBC response on days 7, 16 and 28. Values reported are the ELISA absorbance value at a serum dilution of 1/50. Error bars indicate standard deviation.

As shown in FIG. 11, a single treatment with 7F1-G2b at 25 µg/mouse (1.25 mg/kg) suppressed the IgG immune response by 87% on Day 16 and complete suppression was obtained with 50 or 100 µg doses at Day 16. At Day 28, 50 µg/mouse suppressed the IgG response by 89%, and 100 µg/mouse suppressed completely. Note that MR1 was used as a positive control for immunosuppression at a suboptimal dose of 100 µg/mouse.

3. 7E1-G2b in Preventative Collagen-Induced Arthritis (CIA) Mouse Model

A standard experimental murine model for rheumatoid arthritis, the collagen-induced arthritis model (CIA), was used to determine the effect of 7E1-G2b on prevention of arthritis. DBA/1J male mice (6–8 weeks) were injected with 200 ug of chicken collagen type II (CII) in complete Freund's adjuvant intradermally on day 0. Treatment with 7E1-G2b at 250 µg/dose was administered IP every 4 days starting on day 7. The control group was treated with PBS on the same dosing schedule. All mice were boosted with CII in incomplete Freund's adjuvant on day 21. Mice were observed daily for paw swelling and subjectively scored on a scale of 0–3 with 3 equal to maximum swelling and erythema. Paws were also measured with calipers daily. The clinical score reported was derived by summation of the score of each paw at the time of sacrifice and dividing by the total number of animal in each group. The values reported are the median range of the groups.

Arthritis development, and hence joint inflammation in the mice, was completely inhibited by therapy with 7E1-G2b as shown in Table 1 below. Mice treated with 7E1-G2b were completely free of disease through 90 days.

TABLE 1

Treatment of Collagen-Induced Arthritis

| Tx Group | Arthritis Incidence | Median (Range) Day of onset | Median (Range) Clinical score | Median (Range) Paw measure |
| --- | --- | --- | --- | --- |
| 7E1-G1 | 0/5 | 0 | 0 | 0.075 |
| 7E1-G2b | 0/5 | 0 | 0 | 0.075 |
| PBS control | 4/4 | 30 (27–32) | 3.5 (3–4) | 0.114 (0.110–0.117) |

As demonstrated above, the antibodies of the present invention are potent immunomodulators, with therapeutic uses against a variety of disease. The present invention encompasses chimeric and humanized antibodies as described above with additional conservative amino acid substitutions which have substantially no effect on CD40 binding. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

In one aspect, the present invention is directed to producing the chimeric and/or humanized antibodies as described above by expressing recombinant DNA segments encoding the murine light variable chain and heavy variable chain (or portions thereof), attached to DNA segments encoding the human constant regions. Exemplary DNA sequences designed in accordance with the present invention code for the polypeptide chains comprising all or a portion of the light chain variable region as shown in SEQ ID NO: 1, and/or all or a portion of the heavy chain variable region as shown in SEQ ID NO:2.

Also encompassed within the present invention are the disclosed heavy and light chain variable regions and active or functional parts thereof. The immunologically competent or functional form of the protein or part thereof is also referred to herein as a "light/heavy chain variable region or biologically active portion there of". In the present case, a biologically active portion thereof comprises a portion of said light or heavy chain which, when incorporated into an antibody, still permits the antibody to bind to human CD40.

Specifically encompassed within the present invention are nucleic acid sequences encoding the variable heavy chain and the variable light chain of an antibody of the present invention. For example, nucleotides 1057 through 1422 (SEQ ID NO: 7) of FIG. 13 provide a preferred nucleic acid sequence encoding a variable heavy chain of an antibody of the present invention; nucleotides 1065 through 1388 (SEQ ID NO:8) of FIG. 14 provide a preferred nucleic acid sequence encoding a variable light chain of an antibody of the present invention.

Chimeric antibodies that bind to human CD40 and that comprise polypeptides that are substantially homologous to, or that show substantial sequence identity to, the variable light and heavy chain sequences disclosed herein are also contemplated by the present invention. For example, chimeric antibodies comprising a light chain region that exhibits at least about 85% sequence identity, more preferably at least about 90% sequence identity, even more preferably at least about 95% sequence identity, and most preferably at least about 98% sequence identity with the light chain region as shown in SEQ ID NO:4 are included within the scope of the present invention. More particularly, chimeric antibodies comprising a variable light chain region that exhibits at least about 85% sequence identity, more preferably at least about 90% sequence identity, even more preferably at least about 95% sequence identity, and most preferably at least about 98% sequence identity with the variable light chain region as shown in SEQ ID NO: 1 are also included within the scope of the present invention.

Additionally, chimeric antibodies comprising a heavy chain region that exhibits at least about 85% sequence identity, more preferably at least about 90% sequence identity, even more preferably at least about 95% sequence identity, and most preferably at least about 98% sequence identity with the heavy chain region as shown in SEQ ID NO:3 are included within the scope of the present invention. More particularly, chimeric antibodies comprising a variable heavy chain region that exhibits at least about 85% sequence identity, more preferably at least about 90% sequence identity, even more preferably at least about 95% sequence identity, and most preferably at least about 98% sequence identity with the variable heavy chain region as shown in SEQ ID NO:2 are also included within the scope of the present invention.

The DNA segments typically further include an expression control DNA sequence operably linked to the chimeric antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into an appropriate host, the host is maintained under conditions suitable for high level expression of the nucleotide sequences and, as desired, the collection and purification of the variable light chain, heavy chain, light/heavy chain dimers or intact antibody, binding fragments or other immunoglobulin form may follow. (See, Beychok, S., "Cells of Immunoglobulin Synthesis", Academic Press, N.Y. (1979)). Single chain antibodies may also be produced by joining nucleic acid sequences encoding the VL and VH regions disclosed herein with DNA encoding a polypeptide linker.

Prokaryotic hosts, such as E. coli, and other microbes, such as yeast, may be used to express an antibody of the present invention. In addition to microorganisms, mammalian tissue cell culture may also be used to express and produce the antibodies of the present invention. Eukaryotic cells may be preferred, because a number of suitable host cell lines capable of secreting intact immunoglobulins have been developed in the art, and include the CHO cell lines, various COS cell lines, HeLa cells, myeloma cell lines, and hybridomas. Expression vectors for these cells can include expression control sequences, such as a promoter or enhancer, and necessary processing information sites, such as ribosome binding sites, RNA splice sites, polyadenylation sites, and transcriptional terminator sequences, all known in the art.

The vectors containing the DNA segments of interest (e.g., the heavy and/or light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, e.g., Maniatis, et al., "Molecular Cloning: A Laboratory Manual", Cold Spring Harbor Press (1982)).

Once expressed, the whole antibodies, their dimers, individual light and heavy chains, or other immunoglobulin forms of the present invention, can be purified according to standard procedures in the art, including ammonium sulfate precipitation, affinity columns, column chromatography, gel electrophoresis and the like. Substantially pure immunoglobulins of at least 90 to 95% homogeneity are preferred, and 98 to 99% or more homogeneity are most preferred, for pharmaceutical uses.

The antibodies of the present invention will typically find use in treating antibody mediated and/or T cell mediated disorders. Typical disease states suitable for treatment include graft versus host disease and transplant rejection, and auto immune diseases such as Type I diabetes, psoriasis, multiple sclerosis, rheumatoid arthritis, systemic lupus erythematosus, and myesthenia gravis.

The antibodies and pharmaceutical compositions of the present invention are particularly useful for parenteral administration, i.e., subcutaneously, intramuscularly or intravenously. The pharmaceutical compositions for parenteral administration will commonly comprise a solution of the antibody dissolved in an acceptable carrier, preferably an aqueous carrier. A variety of aqueous carriers can be used, all well known in the art, e.g., water, buffered water, saline, glycine and the like. These solutions are sterile and generally free of particulate matter. These pharmaceutical compositions may be sterilized by conventional well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, human albumin, etc.

The compositions containing antibodies of the present invention can be administered for prophylactic and/or therapeutic treatments. In therapeutic application, compositions are administered to a patient already suffering from a disease, in an amount sufficient to cure or at least partially arrest the disease and its complications. An amount adequate to accomplish this is defined as a therapeutically effective dose. Amounts effective for this use will depend upon the severity of the disease state and the general state of the patient's own immune system, and can be determined by one skilled in the art.

In prophylactic applications, compositions containing antibodies of the present invention are administered to a patient not already in the disease state to enhance the patient's resistance (suppress an immune response). Such an amount is defined to be a "prophylactically effective dose". In this use, the precise amounts again depend upon the patient's state of health and general level of immunity. A preferred prophylactic use is for the prevention of transplant rejection, e.g., kidney transplant rejection.

Although the present invention has been described in some detail by way of illustration and example for purposes of clarity and understanding, it will be apparent that certain changes and modifications may be practiced within -the scope of the appended claims.

We claim:

1. A method for suppressing a humoral immune response in a patient comprising the administration of a therapeutically effective dose of a pharmaceutical composition comprising a chimeric antibody which binds to human CD40, wherein said chimeric antibody comprises a light chain and a heavy chain, said light chain comprising an amino acid sequence of SEQ ID NO:4 and said heavy chain comprising an amino acid sequence as shown in SEQ ID NO: 3, or an active portion of said antibody which binds to human CD40.

2. A method for suppressing humoral immune response of claim 1 wherein said humoral immune response is directed against transplant rejection.

3. A method for inducing an immunosuppressive response in a patient comprising the administration of a therapeutically effective dose of a pharmaceutical composition comprising a chimeric antibody which binds to human CD40, wherein said chimeric antibody comprises a light chain and a heavy chain, said light chain comprising an amino acid sequence of SEQ ID NO:4 and said heavy chain comprising an amino acid sequence as shown in SEQ ID NO: 3, or an active portion of said antibody which binds to human CD40.

4. A method for inducing an immunosuppressive response of claim 3 wherein said immunosuppressive response is used to treat an auto immune disease.

5. A method for inducing an immunosuppressive response of claim 4 wherein said autoimmune disease is selected from the group consisting of Type I diabetes, psoriasis, multiple sclerosis, rheumatoid arthritis, systemic lupus erythematosus, and myesthenia gravis.

6. A method for inducing an immunosuppressive response of claim 5 wherein said autoimmune disease is rheumatoid arthritis.

7. A method for inducing an immunosuppressive response of claim 5 wherein said autoimmune disease is systemic lupus erythematosus.

8. A method for inducing an anti-inflammatory response in a patient comprising the administration of a therapeutically effective dose of a pharmaceutical composition comprising a chimeric antibody which binds to human CD40, wherein said chimeric antibody comprises a light chain and a heavy chain, said light chain comprising an amino acid sequence of SEQ ID NO:4 and said heavy chain comprising an amino acid sequence as shown in SEQ ID NO: 3 or an active portion of said antibody which binds to human CD40.

9. A method for inducing an anti-inflammatory response of claim 8 wherein said response is used to treat rheumatoid arthritis.

10. A method for inhibiting the interaction of CD40 and gp39 in a patient comprising the administration of a therapeutically effective dose of a pharmaceutical composition comprising a chimeric antibody which binds to human CD40, wherein said chimeric antibody comprises a light chain and a heavy chain, said light chain comprising an amino acid sequence of SEQ ID NO:4 and said heavy chain comprising an amino acid sequence as shown in SEQ ID NO: 3 or an active portion of said antibody which binds to human CD40.

* * * * *

SEQUENCE LISTING

<160> NUMBER OF SEQ ID NOS: 8

<210> SEQ ID NO 1
<211> LENGTH: 108
<212> TYPE: PRT
<213> ORGANISM: Human and Mouse

<400> SEQUENCE: 1

Asp Ile Val Leu Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
            20                  25                  30

```
Leu His Trp Tyr Gln Gln Lys Ser His Glu Ser Pro Arg Leu Leu Ile
        35                  40                  45

Lys Tyr Ala Ser His Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Ile Tyr Tyr Cys Gln His Gly His Ser Phe Pro Trp
                 85                  90                  95

Thr Phe Gly Gly Gly Thr Lys Leu Glu Ile Lys Arg
            100                 105

<210> SEQ ID NO 2
<211> LENGTH: 122
<212> TYPE: PRT
<213> ORGANISM: Human and Mouse

<400> SEQUENCE: 2

Gln Ile Gln Leu Val Gln Ser Gly Pro Glu Leu Lys Lys Pro Gly Glu
 1               5                  10                  15

Thr Val Arg Ile Ser Cys Lys Ala Ser Gly Tyr Ala Phe Thr Thr Thr
                 20                  25                  30

Gly Met Gln Trp Val Gln Glu Met Pro Gly Lys Gly Leu Lys Trp Ile
            35                  40                  45

Gly Trp Ile Asn Thr His Ser Gly Val Pro Lys Tyr Val Glu Asp Phe
 50                  55                  60

Lys Gly Arg Phe Ala Phe Ser Leu Glu Thr Ser Ala Asn Thr Ala Tyr
 65                  70                  75                  80

Leu Gln Ile Ser Asn Leu Lys Asn Glu Asp Thr Ala Thr Tyr Phe Cys
                 85                  90                  95

Val Arg Ser Gly Asn Gly Asn Tyr Asp Leu Ala Tyr Phe Ala Tyr Trp
            100                 105                 110

Gly Gln Gly Thr Leu Val Thr Val Ser Ala
            115                 120

<210> SEQ ID NO 3
<211> LENGTH: 451
<212> TYPE: PRT
<213> ORGANISM: Human and Mouse

<400> SEQUENCE: 3

Gln Ile Gln Leu Val Gln Ser Gly Pro Glu Leu Lys Lys Pro Gly Glu
 1               5                  10                  15

Thr Val Arg Ile Ser Cys Lys Ala Ser Gly Tyr Ala Phe Thr Thr Thr
                 20                  25                  30

Gly Met Gln Trp Val Gln Glu Met Pro Gly Lys Gly Leu Lys Trp Ile
            35                  40                  45

Gly Trp Ile Asn Thr His Ser Gly Val Pro Lys Tyr Val Glu Asp Phe
 50                  55                  60

Lys Gly Arg Phe Ala Phe Ser Leu Glu Thr Ser Ala Asn Thr Ala Tyr
 65                  70                  75                  80

Leu Gln Ile Ser Asn Leu Lys Asn Glu Asp Thr Ala Thr Tyr Phe Cys
                 85                  90                  95

Val Arg Ser Gly Asn Gly Asn Tyr Asp Leu Ala Tyr Phe Ala Tyr Trp
            100                 105                 110

Gly Gln Gly Thr Leu Val Thr Val Ser Ala Ala Ser Thr Lys Gly Pro
            115                 120                 125
```

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 214
<212> TYPE: PRT
<213> ORGANISM: Human and Mouse

<400> SEQUENCE: 4

Asp Ile Val Leu Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
```

```
                35                  40                  45
Lys Tyr Ala Ser His Ser Ile Ser Gly Ile Pro Ser Arg Phe Ser Gly
    50                  55                  60
Ser Gly Ser Gly Ser Asp Phe Thr Leu Ser Ile Asn Ser Val Glu Pro
65                  70                  75                  80
Glu Asp Val Gly Ile Tyr Tyr Cys Gln His Gly His Ser Phe Pro Trp
                85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 5
<211> LENGTH: 8614
<212> TYPE: DNA
<213> ORGANISM: Human and Mouse

<400> SEQUENCE: 5
gacggatcgg gagatctgct aggtgacctg aggcgcgccg gcttcgaata gccagagtaa      60
ccttttttt taatttttatt ttatttttatt tttgagatgg agtttggcgc cgatctcccg    120
atcccctatg gtcgactctc agtacaatct gctctgatgc cgcatagtta agccagtatc    180
tgctccctgc ttgtgtgttg gaggtcgctg agtagtgcgc gagcaaaatt taagctacaa    240
caaggcaagg cttgaccgac aattgcatga agaatctgct tagggttagg cgttttgcgc    300
tgcttcgcga tgtacgggcc agatatacgg gttgacattg attattgact agttattaat    360
agtaatcaat tacgggtca ttagttcata gcccatatat ggagttccgc gttacataac     420
ttacggtaaa tggcccgcct ggctgaccgc ccaacgaccc ccgcccattg acgtcaataa    480
tgacgtatgt tcccatagta acgccaatag ggactttcca ttgacgtcaa tgggtggact    540
atttacggta aactgcccac ttggcagtac atcaagtgta tcatatgcca agtacgcccc    600
ctattgacgt caatgacggt aaatggcccg cctggcatta tgcccagtac atgaccttat    660
gggactttcc tacttggcag tacatctacg tattagtcat cgctattacc atggtgatgc    720
ggttttggca gtacatcaat gggcgtggat agcggtttga ctcacgggga tttccaagtc    780
tccaccccat tgacgtcaat gggagtttgt tttggcacca aaatcaacgg gactttccaa    840
aatgtcgtaa caactccgcc ccattgacgc aaatgggcgg taggcgtgta cggtgggagg    900
tctatataag cagagctctc tggctaacta gagaacccac tgcttactgg cttatcgaaa    960
ttaatacgac tcactatagg gagacccaag cttggtacca tggactggac ctggagaatc   1020
ctcttcttgg tggcagcagc aacaggtgcc cactcccaga tccagttggt gcaatctgga   1080
```

-continued

```
cctgagctga agaagcctgg agagacagtc aggatctcct gcaaggcttc tgggtatgcc    1140
ttcacaacta ctggaatgca gtgggtgcaa gagatgccag gaaagggttt gaagtggatt    1200
ggctggataa acacccactc tggagtgcca aaatatgtag aagacttcaa gggacggttt    1260
gccttctctt tggaaacctc tgccaacact gcatatttac agataagcaa cctcaaaaat    1320
gaggacacgg ctacgtattt ctgtgtgaga tccgggaatg gtaactatga cctggcctac    1380
tttgcttact ggggccaagg gacactggtc actgtctctg cagctagcac caagggccca    1440
tcggtcttcc ccctggcacc ctcctccaag agcacctctg gggcacagcg gccctgggc    1500 tgcctggtca aggactactt ccccgaaccg gtgacggtgt cgtggaactc aggcgccctg    1560
accagcggcg tgcacacctt cccggctgtc ctacagtcct caggactcta ctccctcagc    1620
agcgtggtga ccgtgccctc cagcagcttg ggcacccaga cctacatctg caacgtgaat    1680
cacaagccca gcaacaccaa ggtggacaag aaagttggtg agaggccagc acagggaggg    1740
agggtgtctg ctggaagcca ggctcagcgc tcctgcctgg acgcatcccg gctatgcagc    1800
cccagtccag ggcagcaagg caggcccgt ctgcctcttc acccggaggc ctctgcccgc    1860
cccactcatg ctcagggaga gggtcttctg gcttttttcc caggctctgg gcaggcacag    1920
gctaggtgcc cctaacccag gccctgcaca caaaggggca ggtgctgggc tcagacctgc    1980
caagagccat atccgggagg accctgcccc tgacctaagc ccacccaaa ggccaaactc    2040 tccactccct cagctcggac accttctctc ctcccagatt ccagtaactc ccaatcttct    2100
ctctgcagag cccaaatctt gtgacaaaac tcacacatgc ccaccgtgcc caggtaagcc    2160
agcccaggcc tcgccctcca gctcaaggcg ggacaggtgc cctagagtag cctgcatcca    2220
gggacaggcc ccagccgggt gctgacacgt ccacctccat ctcttcctca gcacctgaac    2280
tcctgggggg accgtcagtc ttcctcttcc ccccaaaacc caaggacacc ctcatgatct    2340
cccggacccc tgaggtcaca tgcgtggtgg tggacgtgag ccacgaagac cctgaggtca    2400
agttcaactg gtacgtggac ggcgtggagg tgcataatgc caagacaaag ccgcgggagg    2460
agcagtacaa cagcacgtac cgtgtggtca gcgtcctcac cgtcctgcac caggactggc    2520
tgaatggcaa ggagtacaag tgcaaggtct ccaacaaagc cctcccagcc cccatcgaga    2580
aaaccatctc caaagccaaa ggtgggaccc gtggggtgcg agggccacat ggacagaggc    2640
cggctcggcc caccctctgc cctgagagtg accgctgtac caacctctgt ccctacaggg    2700
cagccccgag aaccacaggt gtacaccctg ccccatccc gggatgagct gaccaagaac    2760
caggtcagcc tgacctgcct ggtcaaaggc ttctatccca gcgacatcgc cgtggagtgg    2820
gagagcaatg ggcagccgga gaacaactac aagaccacgc ctcccgtgct ggactccgac    2880
ggctccttct tcctctacag caagctcacc gtggacaaga gcaggtggca gcaggggaac    2940
gtcttctcat gctccgtgat gcatgaggct ctgcacaacc actacacgca gaagagcctc    3000
tccctgtctc cgggtaaatg agtgcgacgg ccggcaagcc cccgctcccc gggctctcgc    3060
ggtcgcacga ggatgcttgg cacgtacccc ctgtacatac ttcccgggcg cccagcatgg    3120
aaataaagca cccagcgctg ccctgggccc ctgcgagact gtgatggttc tttccacggg    3180
tcaggccgag tctgaggcct gagtggcatg agggaggcag agcgggtccc actgtcccca    3240
cactggccca ggctgtgcag gtgtgcctgg gcccctagg gtggggctca gccaggggct    3300 gcctcggca gggtggggga tttgccagcg tggccctccc tccagcagca cctgccctgg    3360
gctgggccac gggaagccct aggagcccct ggggacagac acacagcccc tgcctctgta    3420
ggagactgtc ctgttctgtg agcgcccctg tcctcccgac ctccatgccc actcgggggc    3480
```

```
atgcctagtc catgtgcgta gggacaggcc ctccctcacc catctacccc cacggcacta    3540
acccctggct gccctgccca gcctcgcacc cgcatgggga cacaaccgac tccggggaca    3600
tgcactctcg ggcctgtgg agggactggt gcagatgccc acacacacac tcagcccaga    3660
cccgttcaac aaaccccgca ctgaggttgg ccggccacac ggccaccaca cacacacgtg    3720
cacgcctcac acacggagcc tcacccgggc gaactgcaca gcacccagac cagagcaagg    3780
tcctcgcaca cgtgaacact cctcggacac aggcccccac gagccccacg cggcacctca    3840
aggcccacga gcctctcggc agcttctcca catgctgacc tgctcagaca aacccagccc    3900
tcctctcaca agggtgcccc tgcagccgcc acacacacac agggggatcac acaccacgtc    3960 acgtccctgg ccctggccca cttcccagtg ccgcccttcc ctgcaggacg gatcagcctc    4020
gactgtgcct tctagttgcc agccatctgt tgtttgcccc tcccccgtgc cttccttgac    4080
cctggaaggt gccactccca ctgtcctttc ctaataaaat gaggaaattg catcgcattg    4140
tctgagtagg tgtcattcta ttctgggggg tggggtgggg caggacagca agggggagga    4200
ttgggaagac aatagcaggc atgctgggga tgcggtgggc tctatggctt ctgaggcgga    4260
aagaaccagc tggggctcta gggggtatcc ccacgcgccc tgtagcggcg cattaagcgc    4320
ggcgggtgtg gtggttacgc gcagcgtgac cgctacactt gccagcgccc tagcgcccgc    4380
tcctttcgct ttcttcccct cctttctcgc cacgttcgcc gggcctctca aaaagggaa    4440 aaaaagcatg catctcaatt agtcagcaac catagtcccg ccctaactc cgcccatccc    4500 gcccctaact ccgcccagtt ccgcccattc tccgcccat ggctgactaa ttttttttat    4560
ttatgcagag gccgaggccg cctcggcctc tgagctattc cagaagtagt gaggaggctt    4620
ttttggaggc ctaggcttt gcaaaaagct tggacagctc agggctgcga tttcgcgcca    4680
aacttgacgg caatcctagc gtgaaggctg gtaggatttt atccccgctg ccatcatggt    4740
tcgaccattg aactgcatcg tcgccgtgtc ccaaaatatg gggattggca agaacggaga    4800
cctaccctgg cctccgctca ggaacgagtt caagtactcc caagaatga ccacaacctc    4860 ttcagtggaa ggtaaacaga atctggtgat tatgggtagg aaaacctggt tctccattcc    4920
tgagaagaat cgacctttaa aggacagaat taatatagtt ctcagtagag aactcaaaga    4980
accaccacga ggagctcatt ttcttgccaa agtttggat gatgccttaa gacttattga    5040
acaaccggaa ttggcaagta aagtagacat ggtttggata gtcggaggca gttctgttta    5100
ccaggaagcc atgaatcaac caggccacct tagactcttt gtgacaagga tcatgcagga    5160
atttgaaagt gacacgtttt tcccagaaat tgatttgggg aaatataaac ttctcccaga    5220
atacccaggc gtcctctctg aggtccagga ggaaaaggc atcaagtata agtttgaagt    5280
ctacgagaag aaagactaac aggaagatgc tttcaagttc tctgctcccc tcctaaagct    5340
atgcattttt ataagaccat gggacttttg ctggctttag atctctttgt gaaggaacct    5400
tacttctgtg gtgtgacata attggacaaa ctacctacag agatttaaag ctctaaggta    5460
aatataaaat ttttaagtgt ataatgtgtt aaactactga ttctaattgt ttgtgtattt    5520
tagattccaa cctatggaac tgatgaatgg gagcagtggt ggaatgcctt taatgaggaa    5580
aacctgtttt gctcagaaga aatgccatct agtgatgatg aggctactgc tgactctcaa    5640
cattctactc ctccaaaaaa gaagagaaag gtagaagacc ccaaggactt tccttcagaa    5700
ttgctaagtt ttttgagtca tgctgtgttt agtaatagaa ctcttgcttg ctttgctatt    5760
tacaccacaa aggaaaaagc tgcactgcta tacaagaaaa ttatggaaaa atattctgta    5820
```

```
acctttataa gtaggcataa cagttataat cataacatac tgtttttttct tactccacac    5880
aggcatagag tgtctgctat taataactat gctcaaaaat tgtgtaccttt tagcttttta    5940
atttgtaaag gggttaataa ggaatatttg atgtatagtg ccttgactag agatcataat    6000
cagccatacc acatttgtag aggttttact tgctttaaaa aacctcccac acctcccct     6060
gaacctgaaa cataaaatga atgcaattgt tgtttgttaac ttgtttattg cagcttataa    6120
tggttacaaa taaagcaata gcatcacaaa tttcacaaat aaagcatttt tttcactgca    6180
ttctagttgt ggtttgtcca aactcatcaa tgtatcttat catgtctgga tcggctggat    6240
gatcctccag cgcggggatc tcatgctgga gttcttcgcc cacccaact tgtttattgc     6300
agcttataat ggttacaaat aaagcaatag catcacaaat ttcacaaata aagcattttt    6360
ttcactgcat tctagttgtg gtttgtccaa actcatcaat gtatcttatc atgtctgtat    6420
accgtcgacc tctagctaga gcttggcgta atcatggtca tagctgtttc ctgtgtgaaa    6480
ttgttatccg ctcacaattc cacacaacat acgagccgga agcataaagt gtaaagcctg    6540
ggtgcctaa tgagtgagct aactcacatt aattgcgttg cgctcactgc ccgctttcca     6600
gtcgggaaac ctgtcgtgcc agctgcatta atgaatcggc caacgcgcgg ggagaggcgg    6660
tttgcgtatt gggcgctctt ccgcttcctc gctcactgac tcgctgcgct cggtcgttcg    6720
gctgcggcga gcggtatcag ctcactcaaa ggcggtaata cggttatcca cagaatcagg    6780
ggataacgca ggaaagaaca tgtgagcaaa aggccagcaa aaggccagga accgtaaaaa    6840
ggccgcgttg ctggcgtttt tccataggct ccgcccccct gacgagcatc acaaaaatcg    6900
acgctcaagt cagaggtggc gaaacccgac aggactataa agataccagg cgtttccccc    6960
tggaagctcc ctcgtgcgct ctcctgttcc gaccctgccg cttaccggat acctgtccgc    7020
cttctccct tcgggaagcg tggcgctttc tcaatgctca cgctgtaggt atctcagttc     7080
ggtgtaggtc gttcgctcca agctgggctg tgtgcacgaa ccccccgttc agcccgaccg    7140
ctgcgcctta tccggtaact atcgtcttga gtccaacccg gtaagacacg acttatcgcc    7200
actggcagca gccactggta acaggattag cagagcgagg tatgtaggcg gtgctacaga    7260
gttcttgaag tggtggccta actacggcta cactagaagg acagtatttg gtatctgcgc    7320
tctgctgaag ccagttacct tcggaaaaag agttggtagc tcttgatccg gcaaacaaac    7380
caccgctggt agcggtggtt tttttgtttg caagcagcag attacgcgca gaaaaaagg     7440
atctcaagaa gatcctttga tcttttctac ggggtctgac gctcagtgga acgaaaactc    7500
acgttaaggg attttggtca tgagattatc aaaaaggatc ttcacctaga tccttttaaa    7560
ttaaaaatga agttttaaat caatctaaag tatatatgag taaacttggt ctgacagtta    7620
ccaatgctta atcagtgagg cacctatctc agcgatctgt ctatttcgtt catccatagt    7680
tgcctgactc cccgtcgtgt agataactac gatacgggag gcttaccat ctggccccag     7740
tgctgcaatg ataccgcgag acccacgctc accggctcca gatttatcag caataaacca    7800
gccagccgga agggccgagc gcagaagtgg tcctgcaact ttatccgcct ccatccagtc    7860
tattaattgt tgccgggaag ctagagtaag tagttcgcca gttaatagtt tgcgcaacgt    7920
tgttgccatt gctacaggca tcgtggtgtc acgctcgtcg tttggtatgg cttcattcag    7980
ctccggttcc caacgatcaa ggcgagttac atgatccccc atgttgtgca aaaagcggt     8040
tagctccttc ggtcctccga tcgttgtcag aagtaagttg gccgcagtgt tatcactcat    8100
ggttatggca gcactgcata attctcttac tgtcatgcca tccgtaagat gcttttctgt    8160
gactggtgag tactcaacca agtcattctg agaatagtgt atgcggcgac cgagttgctc    8220
```

-continued

```
ttgcccggcg tcaatacggg ataataccgc gccacatagc agaactttaa aagtgctcat   8280
cattggaaaa cgttcttcgg ggcgaaaact ctcaaggatc ttaccgctgt tgagatccag   8340
ttcgatgtaa cccactcgtg cacccaactg atcttcagca tcttttactt tcaccagcgt   8400
ttctgggtga gcaaaaacag gaaggcaaaa tgccgcaaaa aagggaataa gggcgacacg   8460
gaaatgttga atactcatac tcttcctttt tcaatattat tgaagcattt atcagggtta   8520
ttgtctcatg agcggataca tatttgaatg tatttagaaa aataaacaaa taggggttcc   8580
gcgcacattt ccccgaaaag tgccacctga cgtc                              8614

<210> SEQ ID NO 6
<211> LENGTH: 8858
<212> TYPE: DNA
<213> ORGANISM: Human and Mouse

<400> SEQUENCE: 6
gacggatcgg gagatctgct agcccgggtg acctgaggcg cgccggcttc gaatagccag     60 agtaacctt ttttttaatt ttattttatt ttatttttga gatggagttt ggcgccgatc    120
tcccgatccc ctatggtcga ctctcagtac aatctgctct gatgccgcat agttaagcca    180
gtatctgctc cctgcttgtg tgttggaggt cgctgagtag tgcgcgagca aaatttaagc    240
tacaacaagg caaggcttga ccgacaattg catgaagaat ctgcttaggg ttaggcgttt    300
tgcgctgctt cgcgatgtac gggccagata tacgcgttga cattgattat tgactagtta    360
ttaatagtaa tcaattacgg ggtcattagt tcatagccca tatatggagt tccgcgttac    420
ataacttacg gtaaatggcc cgcctggctg accgcccaac gacccccgcc cattgacgtc    480
aataatgacg tatgttccca tagtaacgcc aatagggact ttccattgac gtcaatgggt    540
ggactattta cggtaaactg cccacttggc agtacatcaa gtgtatcata tgccaagtac    600
gccccctatt gacgtcaatg acggtaaatg gcccgcctgg cattatgccc agtacatgac    660
cttatgggac tttcctactt ggcagtacat ctacgtatta gtcatcgcta ttaccatggt    720
gatgcggttt tggcagtaca tcaatgggcg tggatagcgg tttgactcac ggggatttcc    780
aagtctccac cccattgacg tcaatgggag tttgttttgg caccaaaatc aacgggactt    840
tccaaaatgt cgtaacaact ccgccccatt gacgcaaatg ggcggtaggc gtgtacggtg    900
ggaggtctat ataagcagag ctctctggct aactagagaa cccactgctt actggcttat    960
cgaaattaat acgactcact ataggagac ccaagcttgg taccatggaa gccccagctc   1020
agcttctctt cctcctgcta ctctggctcc cagataccac cggagacatt gttctgactc   1080
agtctccagc caccctgtct gtgactccag gagatagagt ctctctttcc tgcagggcca   1140
gccagagtat tagcgactac ttacactggt atcaacaaaa atcacatgag tctccaaggc   1200
ttctcatcaa atatgcttcc cattccatct ctgggatccc ctccaggttc agtggcagtg   1260
gatcagggtc agatttcact ctcagtatca acagtgtgga acctgaagat gttggaattt   1320
attactgtca acatggtcac agctttccgt ggacgttcgg tggaggcacc aagctggaaa   1380
tcaaacgtaa gtctcgagtc tctagataac cggtcaatcg gtcaatcgat tggaattcta   1440
aactctgagg gggtcggatg acgtggccat tctttgccta agcattgag tttactgcaa   1500 ggtcagaaaa gcatgcaaag ccctcagaat ggctgcaaag agctccaaca aaacaattta   1560
gaactttatt aaggaatagg gggaagctag gaagaaactc aaaacatcaa gattttaaat   1620
acgcttcttg gtctccttgc tataattatc tgggataagc atgctgtttt ctgtctgtcc   1680
```

-continued

```
ctaacatgcc cttatccgca aacaacacac ccaagggcag aactttgtta cttaaacacc    1740
atcctgtttg cttctttcct caggaactgt ggctgcacca tctgtcttca tcttcccgcc    1800
atctgatgag cagttgaaat ctggaactgc ctctgttgtg tgcctgctga ataacttcta    1860
tcccagagag gccaaagtac agtggaaggt ggataacgcc ctccaatcgg gtaactccca    1920
ggagagtgtc acagagcagg acagcaagga cagcacctac agcctcagca gcaccctgac    1980
gctgagcaaa gcagactacg agaaacacaa agtctacgcc tgcgaagtca cccatcaggg    2040
cctgagctcg cccgtcacaa agagcttcaa caggggagag tgttagaggg agaagtgccc    2100
ccacctgctc ctcagttcca gcctgacccc ctcccatcct ttggcctctg accctttttc    2160
cacaggggac ctaccoctat tgcggtcctc cagctcatct ttcacctcac ccccctcctc    2220
ctccttggct ttaattatgc taatgttgga ggagaatgaa taaataaagt gaatctttgc    2280
acctgtggtt tctctctttc ctcatttaat aattattatc tgttgtttta ccaactactc    2340
aatttctctt ataagggact aaatatgtag tcatcctaag gcacgtaacc atttataaaa    2400
atcatccttc attctatttt accctatcat cctctgcaag acagtcctcc ctcaaaccca    2460
caagccttct gtcctcacag tcccctgggc catggtagga gagacttgct tccttgtttt    2520
cccctcctca gcaagccctc atagtccttt ttaagggtga caggtcttac agtcatatat    2580
cctttgattc aattccctga gaatcaacca aagcaaattt ttcaaaagaa gaaacctgct    2640
ataaagagaa tcattcattg caacatgata taaaataaca acacaataaa agcaattaaa    2700
taaacaaaca atagggaaat gtttaagttc atcatggtac ttagacttaa tggaatgtca    2760
tgccttattt acatttttaa acaggtactg agggactcct gtctgccaag ggccgtattg    2820
agtactttcc acaacctaat ttaatccaca ctatactgtg agattaaaaa cattcattaa    2880
aatgttgcaa aggttctata aagctgagag acaaatatat tctataactc agcaatccca    2940
cttctagatg actgagtgtc cccacccacc aaaaaactat gcaagaatgt tcaaagcagc    3000
tttatttaca aaagccaaaa attggaaata gcccgattgt ccaacaatag aatgagttat    3060
taaactgtgg tatgtttata cattagaata cccaatgagg agaattaaca agctacaact    3120
atacctactc acacagatga atctcataaa aataatgtta cataagagaa actcaatgca    3180
aaagatatgt tctgtatgtt ttcatccata taaagttcaa aaccaggtaa aaataaagtt    3240
agaaatttgg atggaaatta ctcttagctg ggggtgggcg agttagtgcc tgggagaaga    3300
caagaagggg cttctgggt cttggtaatg ttctgttcct cgtgtggggt tgtgcagtta    3360
tgatctgtgc actgttctgt atacacatta tgcttcaaaa taacttcaca taaagaacat    3420
cttataccca gttaatagat agaagaggaa taagtaatag gtcaagacca acgcagctgg    3480
taagtggggg cctgggatca aatagctacc tgcctaatcc tgcccwcttg agccctgaat    3540
gagtctgcct tccagggctc aaggtgctca acaaaacaac aggcctgcta ttttcctggc    3600
atctgtgccc tgtttggcta gctaggagca cacatacata gaaattaaat gaaacagacc    3660
ttcagcaagg ggacagagga cagaattaac cttgcccaga cactggaaac ccatgtatga    3720
acactcacat gtttgggaag ggggaagggc acatgtaaat gaggactctt cctcattcta    3780
tggggcactc tggccctgcc cctctcagct actcatccat ccaacacacc tttctaagta    3840
cctctctctg cctacactct gaagggttc aggagtaact aacacagcat cccttccctc    3900
aaatgactga caatccettt gtcctgcttt gttttctttt ccagtcagta ctgggaaagt    3960
ggggaaggac agtcatggag aaactacata aggaagcacc ttgcccttct gcctcttgag    4020
aatgttgatg agtatcaaat ctttcaaact ttggaggttt gagtaggggt gagactcagt    4080
```

```
aatgtccctt ccaatgacat gaacttgctc actcatccct gggggccaaa ttgaacaatc   4140
aaaggcaggc ataatccagt tatgaattct tgcggccgct tgctagcttc acgtgttgga   4200
tccaaccgcg gaagggccct attctatagt gtcacctaaa tgctagagct cgctgatcag   4260
cctcgactgt gccttctagt tgccagccat ctgttgtttg ccctcccccc gtgccttcct   4320
tgaccctgga agtgccact  cccactgtcc tttcctaata aaatgaggaa attgcatcgc   4380
attgtctgag taggtgtcat tctattctgg ggggtggggt ggggcaggac agcaaggggg   4440
aggattggga agacaatagc aggcatgctg gggatgcggt gggctctatg gcttctgagg   4500
cggaaagaac cagctgggc  tctaggggt  atccccacgc gccctgtagc ggcgcattaa   4560
gcgcggcggg tgtggtggtt acgcgcagcg tgaccgctac acttgccagc gccctagcgc   4620
ccgctccttt cgctttcttc ccttcctttc tcgccacgtt cgccgggcct ctcaaaaaag   4680
ggaaaaaaag catgcatctc aattagtcag caaccatagt cccgcccta  actccgccca   4740 tcccgcccct aactccgccc agttccgccc attctccgcc ccatggctga ctaatttttt   4800
ttatttatgc agaggccgag gccgcctcgg cctctgagct attccagaag tagtgaggag   4860
gcttttttgg aggcctaggc ttttgcaaaa agcttggaca gctcagggct gcgatttcgc   4920
gccaaacttg acggcaatcc tagcgtgaag gctggtagga ttttatcccc gctgccatca   4980
tggttcgacc attgaactgc atcgtcgccg tgtcccaaaa tatgggatt  ggcaagaacg   5040 gagacctacc ctggcctccg ctcaggaacg agttcaagta cttccaaaga atgaccacaa   5100
cctcttcagt ggaaggtaaa cagaatctgg tgattatggg taggaaaacc tggttctcca   5160
ttcctgagaa gaatcgacct ttaaaggaca gaattaatat agttctcagt agagaactca   5220
aagaaccacc acgaggagct cattttcttg ccaaaagttt ggatgatgcc ttaagactta   5280
ttgaacaacc ggaattggca agtaaagtag acatggttg  gatagtcgga ggcagttctg   5340
tttaccagga agccatgaat caaccaggcc accttagact ctttgtgaca aggatcatgc   5400
aggaatttga aagtgacacg ttttttcccag aaattgattt ggggaaatat aaacttctcc   5460
cagaataccc aggcgtcctc tctgaggtcc aggaggaaaa aggcatcaag tataagtttg   5520
aagtctacga gaagaaagac taacaggaag atgctttcaa gttctctgct cccctcctaa   5580
agctatgcat ttttataaga ccatgggact tttgctggct ttagatctct tgtgaagga   5640 accttacttc tgtggtgtga cataattgga caaactacct acagagattt aaagctctaa   5700
ggtaaatata aaatttttaa gtgtataatg tgttaaacta ctgattctaa ttgtttgtgt   5760
attttagatt ccaacctatg gaactgatga atgggagcag tggtggaatg ccttaatga   5820 ggaaaacctg ttttgctcag aagaaatgcc atctagtgat gatgaggcta ctgctgactc   5880
tcaacattct actcctccaa aaagaagag  aaggtagaa  gaccccaagg actttccttc   5940
agaattgcta agttttttga gtcatgctgt gtttagtaat agaactcttg cttgctttgc   6000 tatttcacacc acaaaggaaa aagctgcact gctatacaag aaaattatgg aaaaatattc   6060 tgtaacccttt ataagtaggc ataacagtta taatcataac atactgtttt ttcttactcc   6120
acacaggcat agagtgtctg ctattaataa ctatgctcaa aaattgtgta cctttagctt   6180
tttaatttgt aaagggtta  ataaggaata tttgatgtat agtgccttga ctagagatca   6240
taatcagcca taccacattt gtagaggttt tacttgcttt aaaaaacctc ccacacctcc   6300
ccctgaacct gaaacataaa atgaatgcaa ttgttgttgt taacttgttt attgcagctt   6360
ataatggtta caaataaagc aatagcatca caaatttcac aaataaagca ttttttttcac   6420
```

-continued

```
tgcattctag ttgtggtttg tccaaactca tcaatgtatc ttatcatgtc tggatcggct      6480
ggatgatcct ccagcgcggg gatctcatgc tggagttctt cgcccacccc aacttgttta      6540
ttgcagctta taatggttac aaataaagca atagcatcac aaatttcaca aataaagcat      6600 tttttttcact gcattctagt tgtggtttgt ccaaactcat caatgtatct tatcatgtct      6660
gtataccgtc gacctctagc tagagcttgg cgtaatcatg gtcatagctg tttcctgtgt      6720
gaaattgtta tccgctcaca attccacaca acatacgagc cggaagcata aagtgtaaag      6780 cctgggtgc ctaatgagtg agctaactca cattaattgc gttgcgctca ctgcccgctt      6840
tccagtcggg aaacctgtcg tgccagctgc attaatgaat cggccaacgc gcggggagag      6900
gcggtttgcg tattgggcgc tcttccgctt cctcgctcac tgactcgctg cgctcggtcg      6960
ttcggctgcg gcgagcggta tcagctcact caaaggcggt aatacggtta ccacagaat      7020 caggggataa cgcaggaaag aacatgtgag caaaaggcca gcaaaaggcc aggaaccgta      7080
aaaaggccgc gttgctggcg tttttccata ggctccgccc cctgacgag catcacaaaa       7140 atcgacgctc aagtcagagg tggcgaaacc cgacaggact ataaagatac caggcgtttc      7200
cccctggaag ctccctcgtg cgctctcctg ttccgaccct gccgcttacc ggatacctgt      7260
ccgcctttct cccttcggga agcgtggcgc tttctcaatg ctcacgctgt aggtatctca      7320
gttcggtgta ggtcgttcgc tccaagctgg gctgtgtgca cgaaccccccc gttcagcccg      7380 accgctgcgc cttatccggt aactatcgtc ttgagtccaa cccggtaaga cacgacttat      7440
cgccactggc agcagccact ggtaacagga ttagcagagc gaggtatgta ggcggtgcta      7500
cagagttctt gaagtggtgg cctaactacg gctacactag aaggacagta tttggtatct      7560
gcgctctgct gaagccagtt accttcggaa aaagagttgg tagctcttga tccggcaaac      7620
aaaccaccgc tggtagcggt ggtttttttg tttgcaagca gcagattacg cgcagaaaaa      7680
aaggatctca agaagatcct ttgatctttt ctacggggtc tgacgctcag tggaacgaaa      7740
actcacgtta agggattttg gtcatgagat tatcaaaaag gatcttcacc tagatccttt      7800
taaattaaaa atgaagtttt aaatcaatct aaagtatata tgagtaaact tggtctgaca      7860
gttaccaatg cttaatcagt gaggcaccta tctcagcgat ctgtctattt cgttcatcca      7920
tagttgcctg actccccgtc gtgtagataa ctacgatacg ggagggctta ccatctggcc      7980
ccagtgctgc aatgataccg cgagacccac gctcaccggc tccagattta tcagcaataa      8040
accagccagc cggaagggcc gagcgcagaa gtggtcctgc aactttatcc gcctccatcc      8100
agtctattaa ttgttgccgg gaagctagag taagtagttc gccagttaat agtttgcgca      8160
acgttgttgc cattgctaca ggcatcgtgg tgtcacgctc gtcgtttggt atggcttcat      8220
tcagctccgg ttcccaacga tcaaggcgag ttacatgatc ccccatgttg tgcaaaaaag      8280
cggttagctc cttcggtcct ccgatcgttg tcagaagtaa gttggccgca gtgttatcac      8340
tcatggttat ggcagcactg cataattctc ttactgtcat gccatccgta agatgctttt      8400
ctgtgactgg tgagtactca accaagtcat tctgagaata gtgtatgcgg cgaccgagtt      8460
gctcttgccc ggcgtcaata cgggataata ccgcgccaca tagcagaact ttaaaagtgc      8520
tcatcattgg aaaacgttct tcggggcgaa aactctcaag gatcttaccg ctgttgagat      8580
ccagttcgat gtaacccact cgtgcaccca actgatcttc agcatctttt actttcacca      8640
gcgtttctgg gtgagcaaaa acaggaaggc aaaatgccgc aaaaaaggga ataagggcga      8700
cacggaaatg ttgaatactc atactcttcc ttttcaata ttattgaagc atttatcagg       8760
```

```
gttattgtct catgagcgga tacatatttg aatgtattta gaaaaataaa caaatagggg      8820
ttccgcgcac atttccccga aaagtgccac ctgacgtc                              8858

<210> SEQ ID NO 7
<211> LENGTH: 366
<212> TYPE: DNA
<213> ORGANISM: Human and Mouse

<400> SEQUENCE: 7
cagatccagt tggtgcaatc tggacctgag ctgaagaagc ctggagagac agtcaggatc        60
tcctgcaagg cttctgggta tgccttcaca actactggaa tgcagtgggt gcaagagatg       120
ccaggaaagg gtttgaagtg gattggctgg ataaacaccc actctggagt gccaaaatat       180
gtagaagact tcaagggacg gtttgccttc tctttggaaa cctctgccaa cactgcatat       240
ttacagataa gcaacctcaa aaatgaggac acggctacgt atttctgtgt gagatccggg       300
aatggtaact atgacctggc ctactttgct tactggggcc aagggacact ggtcactgtc       360
tctgca                                                                 366

<210> SEQ ID NO 8
<211> LENGTH: 324
<212> TYPE: DNA
<213> ORGANISM: Human and Mouse

<400> SEQUENCE: 8
gacattgttc tgactcagtc tccagccacc ctgtctgtga ctccaggaga tagagtctct        60
ctttcctgca gggccagcca gagtattagc gactacttac actggtatca acaaaaatca       120
catgagtctc caaggcttct catcaaatat gcttcccatt ccatctctgg gatcccctcc       180
aggttcagtg gcagtggatc agggtcagat ttcactctca gtatcaacag tgtggaacct       240
gaagatgttg gaatttatta ctgtcaacat ggtcacagct ttccgtggac gttcggtgga       300
ggcaccaagc tggaaatcaa acgt                                             324
```